(12) United States Patent
Tamada et al.

(10) Patent No.: US 10,316,102 B2
(45) Date of Patent: Jun. 11, 2019

(54) CAR EXPRESSION VECTOR AND CAR-EXPRESSING T CELLS

(71) Applicant: YAMAGUCHI UNIVERSITY, Yamaguchi (JP)

(72) Inventors: Koji Tamada, Yamaguchi (JP); Yukimi Sakoda, Yamaguchi (JP); Keishi Adachi, Yamaguchi (JP)

(73) Assignee: YAMAGUCHI UNIVERSITY, Yamaguchi (JP)

( * ) Notice: Subject to any disclaimer, the term of this patent is extended or adjusted under 35 U.S.C. 154(b) by 0 days.

(21) Appl. No.: 15/513,870

(22) PCT Filed: Oct. 6, 2015

(86) PCT No.: PCT/JP2015/005080
§ 371 (c)(1),
(2) Date: Mar. 23, 2017

(87) PCT Pub. No.: WO2016/056228
PCT Pub. Date: Apr. 14, 2016

(65) Prior Publication Data
US 2017/0291953 A1 Oct. 12, 2017

(30) Foreign Application Priority Data
Oct. 9, 2014 (JP) .................... 2014-208200

(51) Int. Cl.

| | |
|---|---|
| *A61K 48/00* | (2006.01) |
| *C12N 15/00* | (2006.01) |
| *C12N 15/63* | (2006.01) |
| *C07K 16/28* | (2006.01) |
| *A61K 35/26* | (2015.01) |
| *A61K 35/76* | (2015.01) |
| *C12N 5/10* | (2006.01) |
| *C12N 15/09* | (2006.01) |
| *A61K 35/17* | (2015.01) |
| *C07K 14/52* | (2006.01) |
| *C07K 14/54* | (2006.01) |
| *C07K 14/725* | (2006.01) |
| *C07K 14/705* | (2006.01) |
| *C07K 16/44* | (2006.01) |
| *C12N 5/0783* | (2010.01) |
| *C07K 19/00* | (2006.01) |
| *C07K 14/47* | (2006.01) |

(52) U.S. Cl.
CPC .......... *C07K 16/2887* (2013.01); *A61K 35/17* (2013.01); *A61K 35/26* (2013.01); *A61K 35/76* (2013.01); *C07K 14/521* (2013.01); *C07K 14/5418* (2013.01); *C07K 14/7051* (2013.01); *C07K 14/70517* (2013.01); *C07K 14/70521* (2013.01); *C07K 14/70578* (2013.01); *C07K 16/44* (2013.01); *C12N 5/0636* (2013.01); *C12N 5/10* (2013.01); *C12N 15/00* (2013.01); *C12N 15/09* (2013.01); *C07K 14/47* (2013.01); *C07K 14/54* (2013.01); *C07K 19/00* (2013.01); *C07K 2317/622* (2013.01); *C07K 2319/03* (2013.01); *C07K 2319/74* (2013.01); *C12N 2510/00* (2013.01)

(58) Field of Classification Search
CPC ............ C07K 16/2887; C07K 14/5418; C07K 2319/74; A61K 35/17; A61K 35/26; A61K 35/76; C12N 15/00; C12N 15/09
See application file for complete search history.

(56) References Cited

U.S. PATENT DOCUMENTS

2011/0268766 A1* 11/2011 Beech ................ C12N 15/86
424/277.1
2013/0071414 A1* 3/2013 Dotti ................ C12N 5/0636
424/184.1

(Continued)

FOREIGN PATENT DOCUMENTS

| JP | 2011-4749 | 1/2011 |
| JP | 2014-504294 | 2/2014 |
| JP | 2014-507118 | 3/2014 |

(Continued)

OTHER PUBLICATIONS

Nakazawa, "Gene-modified T-cell Therapy Using Chimeric Antigen Receptor," The Shinshu Medical Journal, 61(4), pp. 197-203, 2013, with partial English translation.

(Continued)

*Primary Examiner* — Quang Nguyen
(74) *Attorney, Agent, or Firm* — Kenneth H. Sonnenfeld; Margaret B. Brivanlou; King & Spalding LLP

(57) ABSTRACT

An object of the present invention is to provide CAR-expressing T cells that coexpress a chimeric antigen receptor (CAR) and a T cell immune function-enhancing factor and have a high immunity-inducing effect and antitumor activity, and to provide a CAR expression vector for the preparation of the CAR-expressing T cells.

A CAR expression vector comprises a nucleic acid encoding a chimeric antigen receptor (CAR) and a nucleic acid encoding a T cell immune function-enhancing factor, wherein the nucleic acid encoding an immune function-enhancing factor is a nucleic acid encoding interleukin-7 and a nucleic acid encoding CCL19, a nucleic acid encoding a dominant negative mutant of SHP-1, or a nucleic acid encoding a dominant negative mutant of SHP-2, or a CAR-expressing T cell introduced with the CAR expression vector are prepared.

19 Claims, 16 Drawing Sheets

Specification includes a Sequence Listing.

(56) References Cited

U.S. PATENT DOCUMENTS

2014/0106449 A1 4/2014 June et al.
2014/0255363 A1* 9/2014 Metelitsa ............... A61K 39/00
424/93.21

FOREIGN PATENT DOCUMENTS

| JP | 2014-516510 | 7/2014 |
|---|---|---|
| WO | WO 2013/051718 | 4/2013 |
| WO | WO 2013/123061 | 8/2013 |
| WO | WO 2013/126729 | 8/2013 |

OTHER PUBLICATIONS

Plas et al., "Direct Regulation of ZAP-70 by SHP-1 in T Cell Antigen Receptor Signaling," Science, 272, pp. 1173-1176, 1996.

Plas et al., "Cutting Edge: The Tyrosine Phosphatase SHP-1 Regulates Thymocyte Positive Selection," The Journal of Immunology, 162, pp. 5680-5684, 1999.

Sakoda et al., "Symposium 4, New Paradigm of Cell and Molecular Machineries for Advanced Immune Therapy," Japanese Journal of Clinical Hematology, 55(6), pp. 651-656, 2014, with partial English translation .

Sato-Hashimoto et al., "Signal Regulatory Protein a Regulates the Homeostasis of T Lymphocytes in the Spleen," The Journal of Immunology, 187, pp. 291-297, 2011.

Siegert et al., "Positive and Negative Regulation of T Cell Responses by Fibroblastic Reticular Cells Within Paracortical Regions of Lymph Nodes," Frontiers in Immunology, pp. 1-10, 2012.

Tamada et al., "Redirecting Gene-Modified T Cells Toward Various Cancer Types Using Tagged Antibodies," Clinical Cancer Research, 18(23), pp. 6436-6445, 2012.

Adachi et al., "IL-7 and CCL19 Expression in CAR-T Cells Improves Immune Cell Infiltration and CAR-T Cell Survival in the Tumor," Nature Biotechnology, pp. 1-40, 2018.

Eto et al., "Antitumor Activity of Interleukin-12 Against Murine Bladder Cancer," The Journal of Urology, 163, pp. 1549-1552, 2000.

Ma et al., Automatic generation of lymphocyte heterogeneity: Division-dependent changes in the expression of CD27, CCR7 and CD45 by activated human naive $CD4^+T$ cells are independently regulated, Immunology and Cell Biology, 82, pp. 67-74, 2004.

Markley et al., "IL-7 and IL-21 are Superior to IL-2 and IL-15 in Promoting Human T Cell-Mediated Rejection of Systemic Lymphoma in Immunodeficient Mice," Blood, 115(17), pp. 3508-3519, 2010.

Robbiani et al., The Leukotriene C4 Transporter MRP1 Regulates CCL19 (MIP-3b, ELC)—Dependent Mobilization of Dendritic Cells to Lymph Nodes, Cell, 103, pp. 757-768, 2000.

Schluns et al., Interleukin-7 mediates the homeostasis of naïve and memory CD8 T cells in vivo, Nature Immunology, pp. 426-432, 2000.

Sven et al., "Combined CCL19/IL-7 Treatment Eradicates Tumors in Murine Models of Lung Cancer," Journal of Thoracic Onocology, 2(8), S615, 2007.

Yang Xu et al., "Closely related T-memory stem cells correlate with in vivo expansion of CAR.CD19-T cells and are preserved by IL-7 and IL-15," Blood vol. 123, No. 24, pp. 3750-3759, Jun. 12, 2014.

Charles A. Janeway, Jr. et al., Immuno Biology, The Immune System in Health and Disease, pp. 7:14-7:15, 1994.

* cited by examiner

[Figure 1]
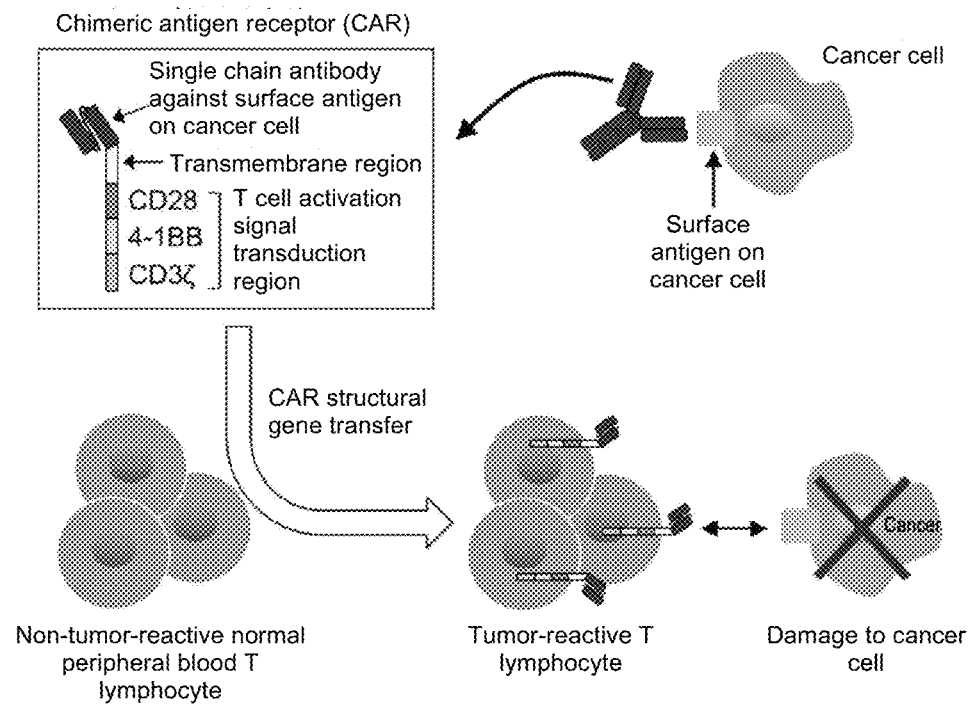
[Figure 2]
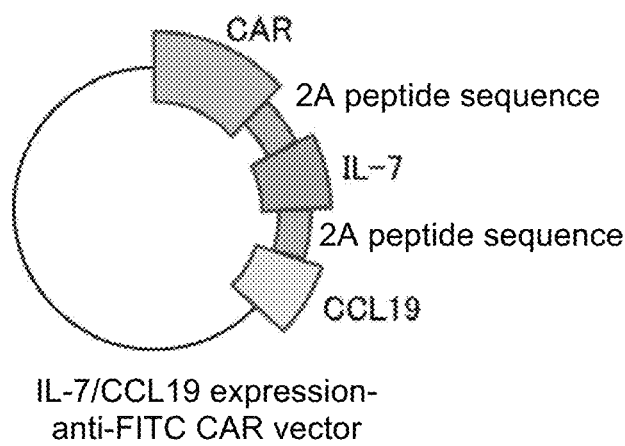
IL-7/CCL19 expression-
anti-FITC CAR vector

[Figure 3]
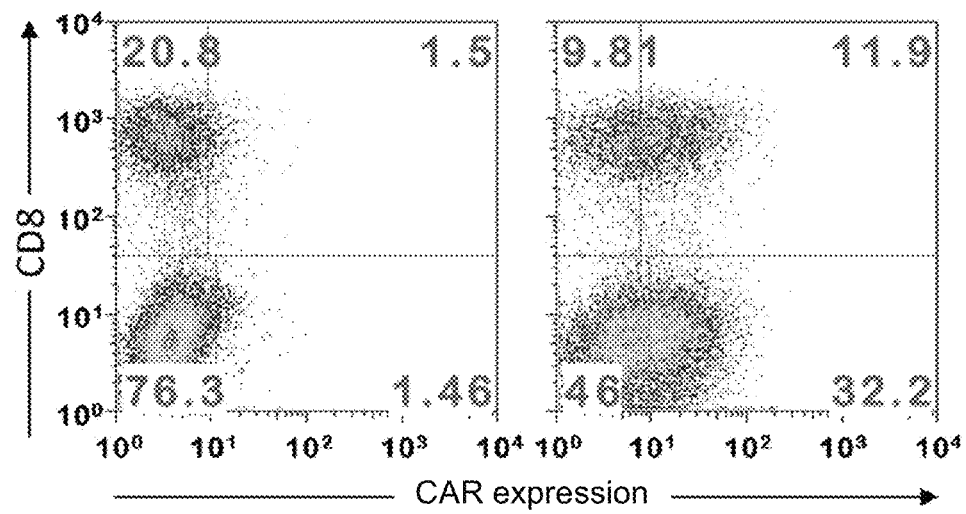
[Figure 4]
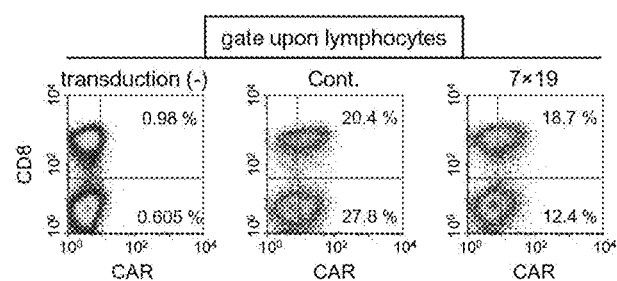
[Figure 5]
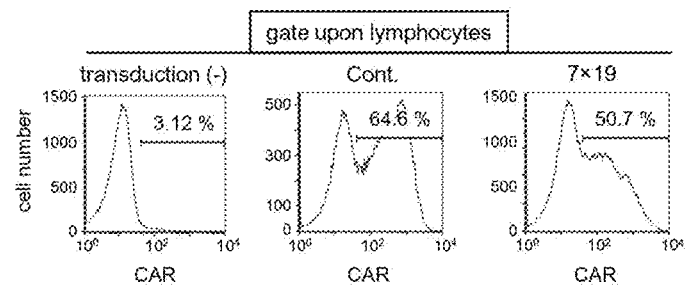

[Figure 6]
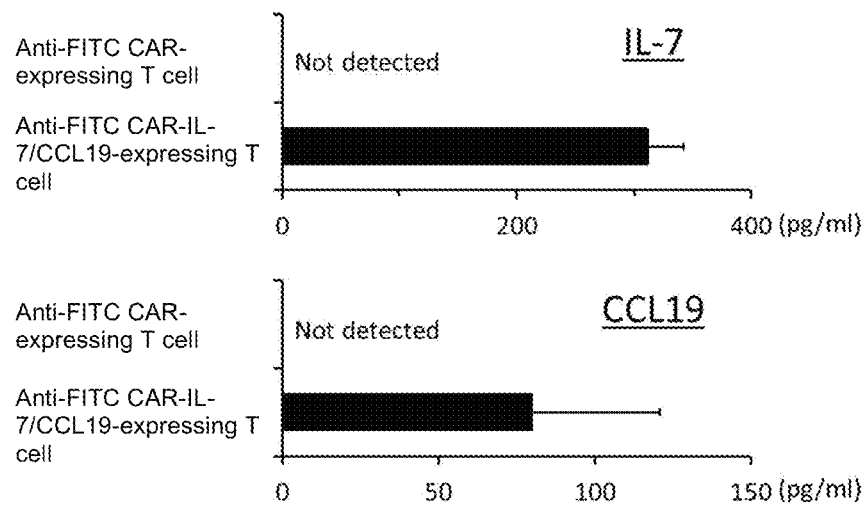
[Figure 7]
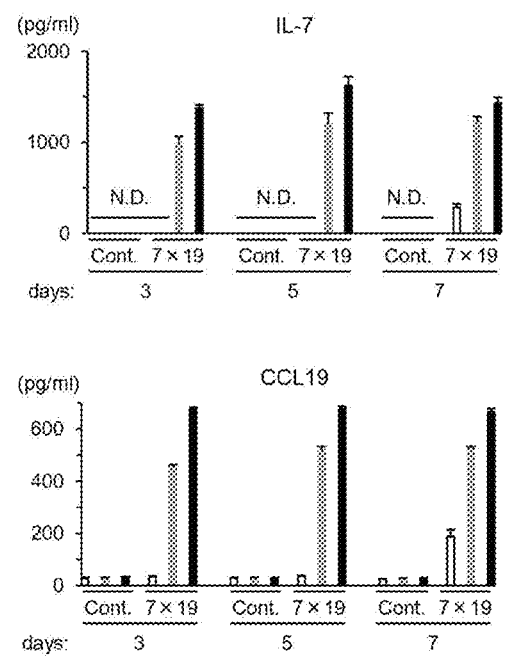

[Figure 8]
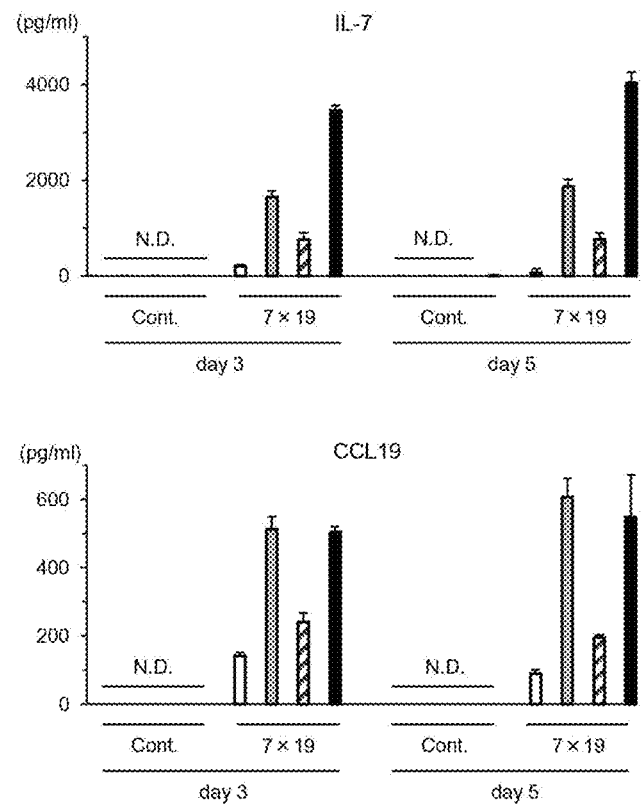
[Figure 9]
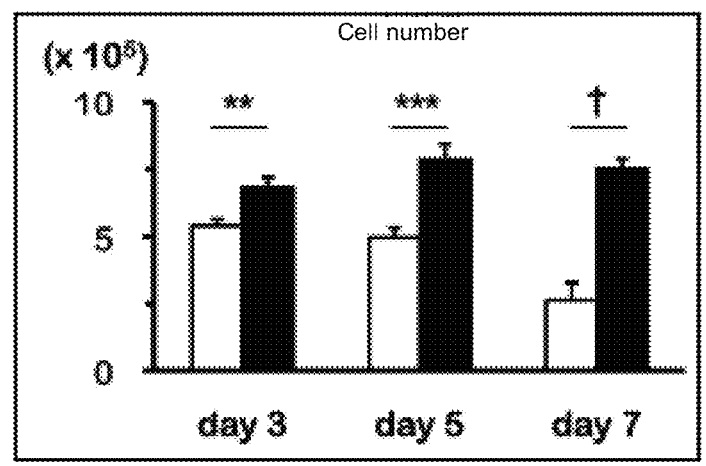

[Figure 10]
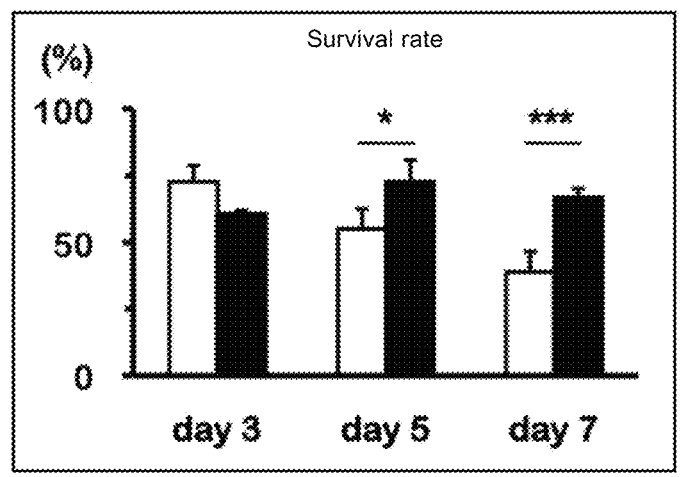
[Figure 11]
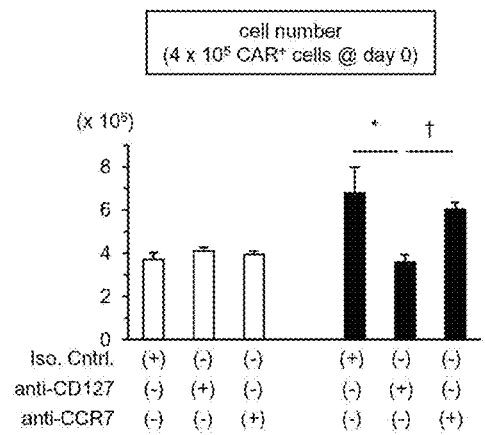

[Figure 12]
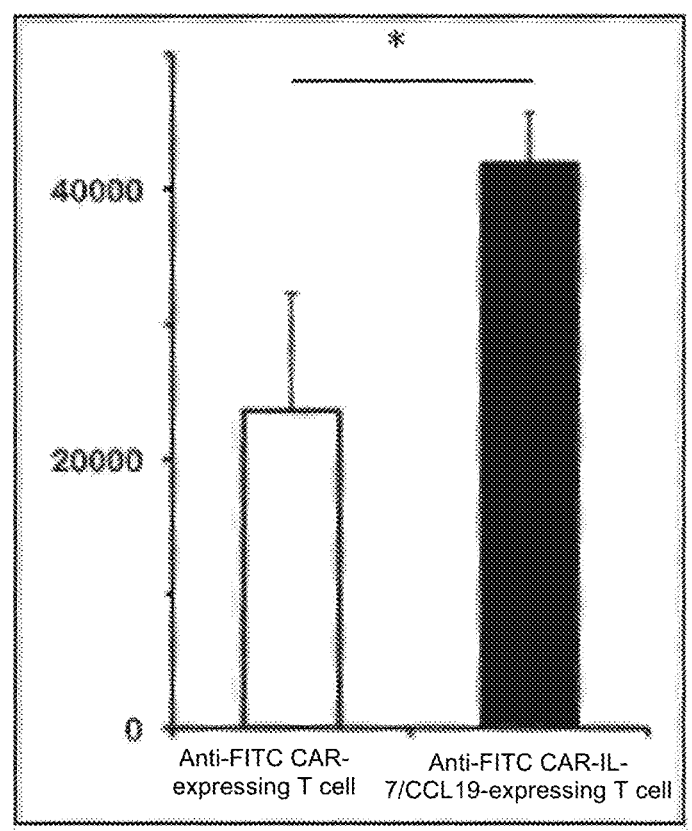

[Figure 13]
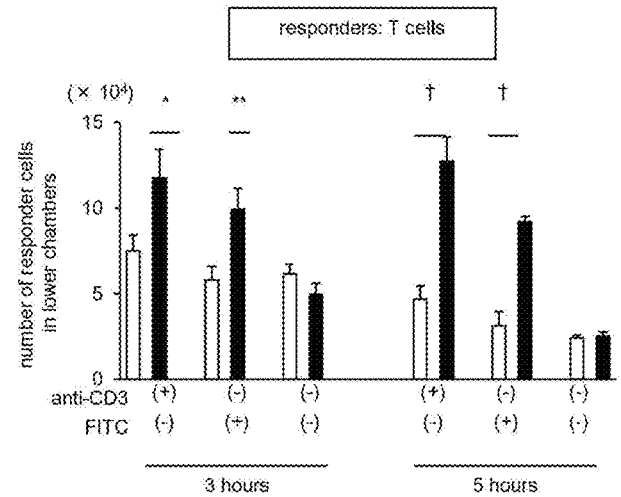
[Figure 14]
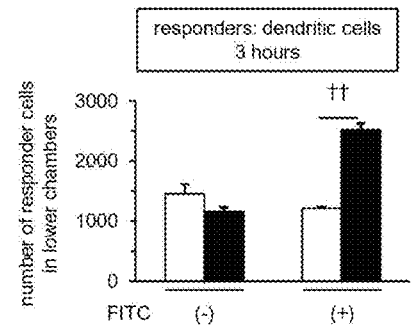
[Figure 15]
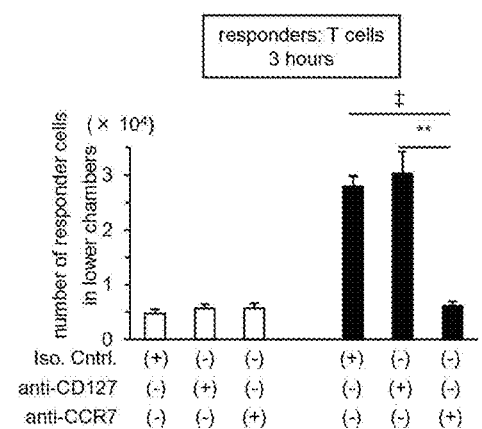

[Figure 16]
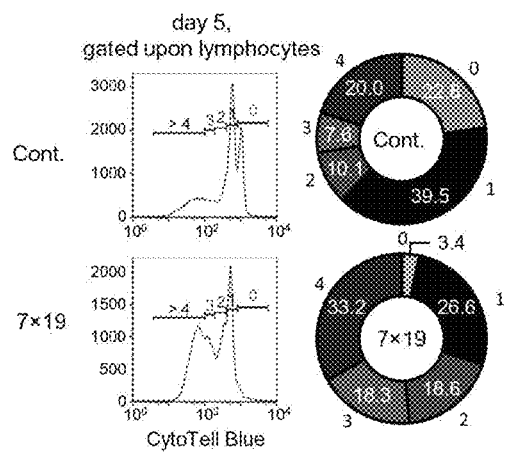
[Figure 17]
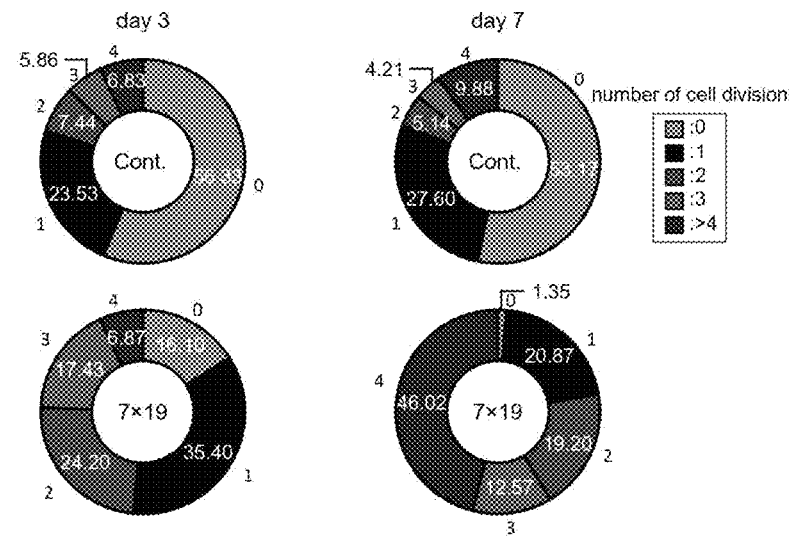

[Figure 18]
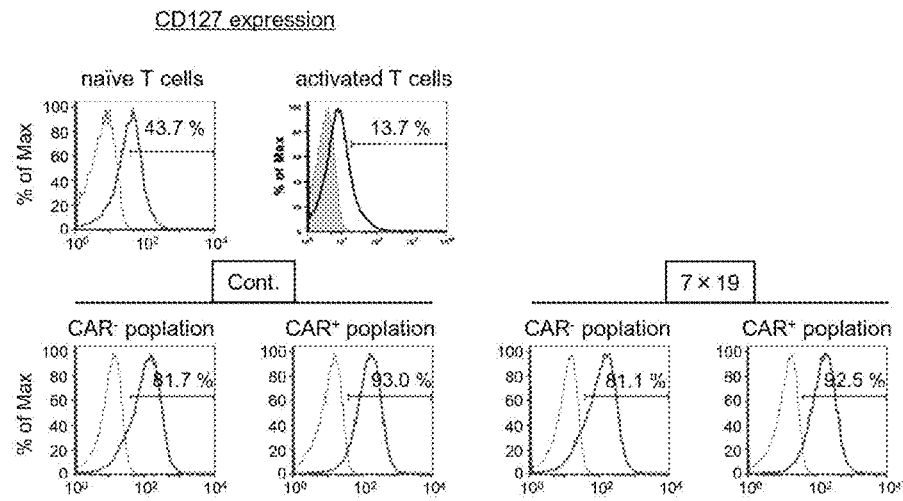
[Figure 19]
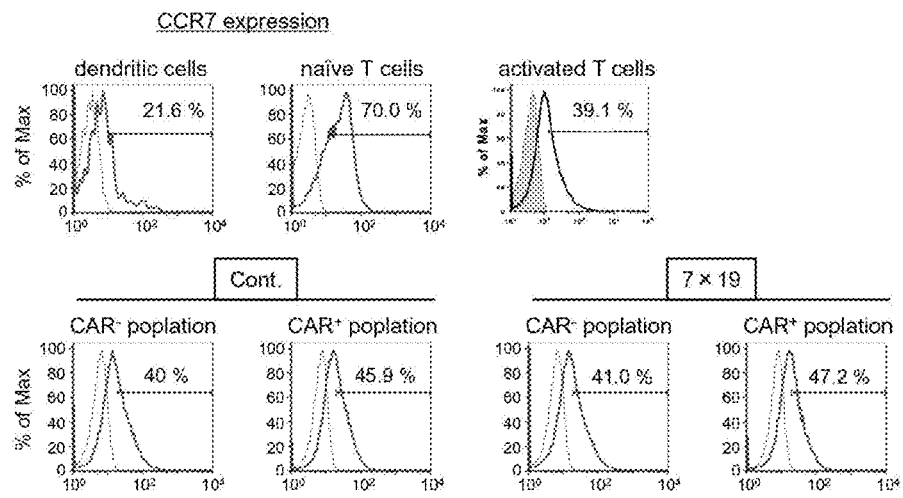

[Figure 20]
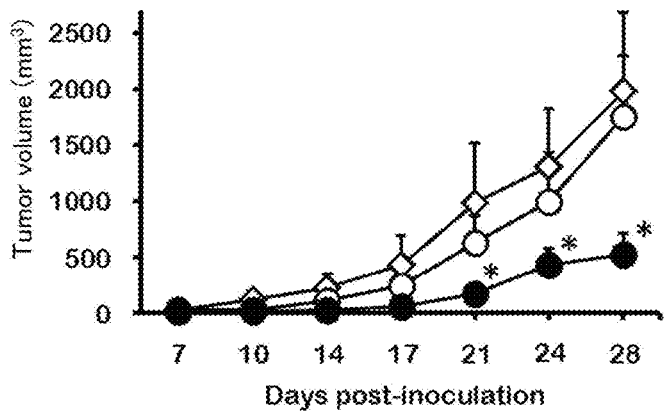
[Figure 21]
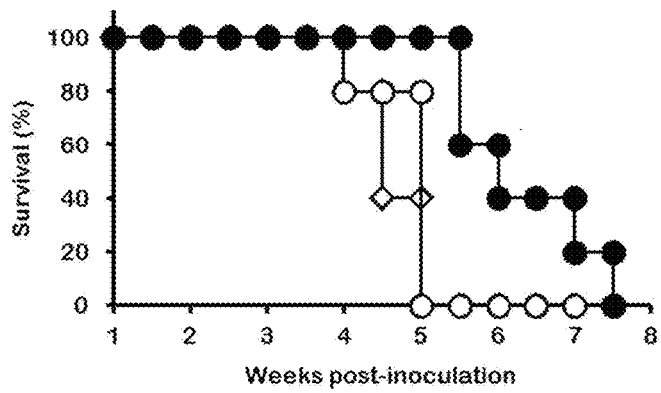
[Figure 22]
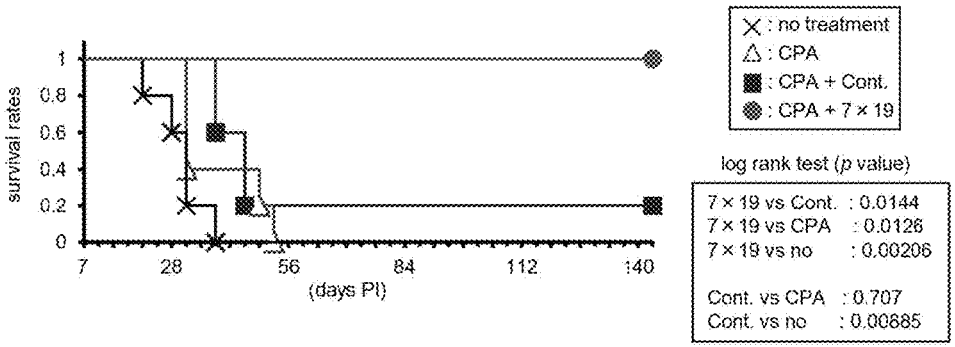

[Figure 23]
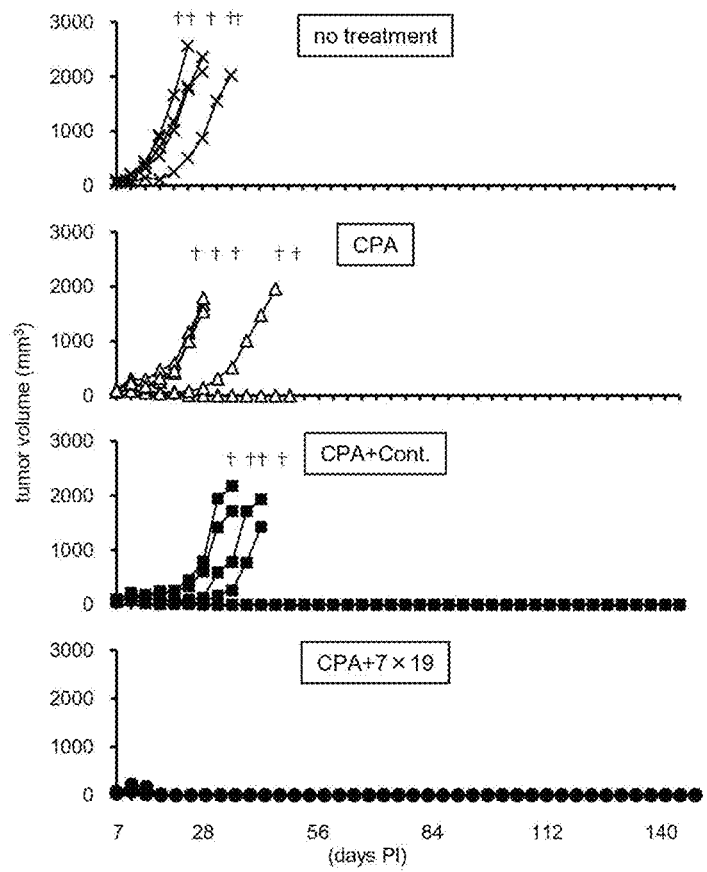
[Figure 24]
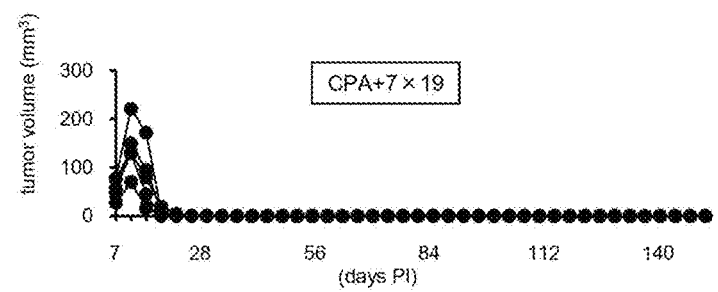

[Figure 25]
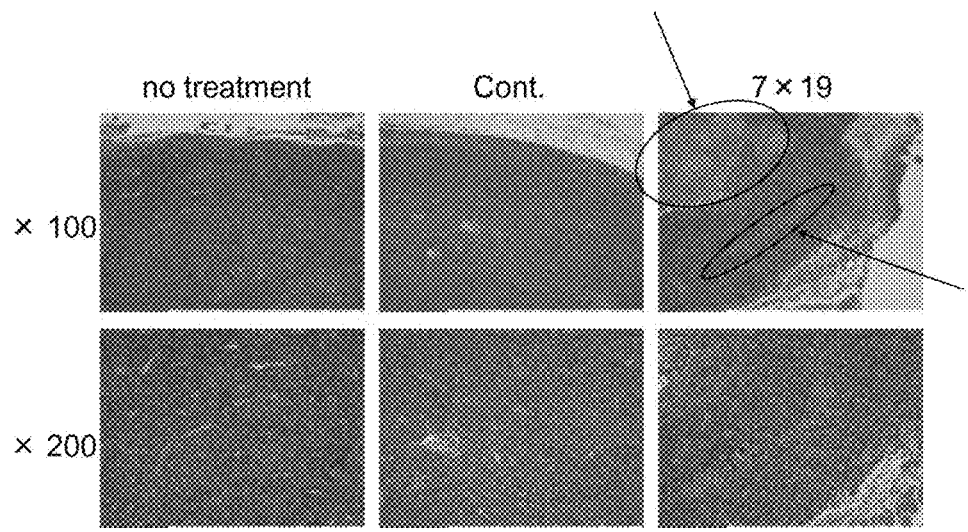
[Figure 26]
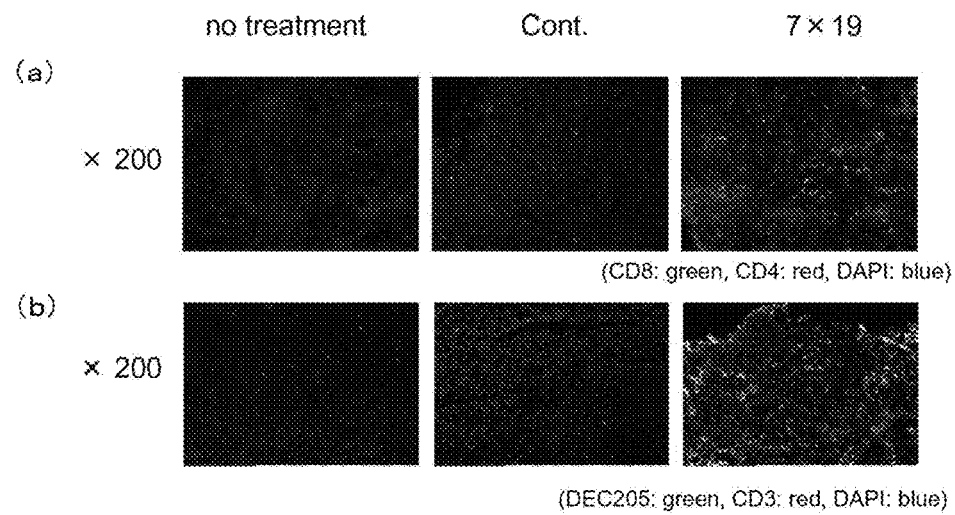
(CD8: green, CD4: red, DAPI: blue)
(DEC205: green, CD3: red, DAPI: blue)

[Figure 27]
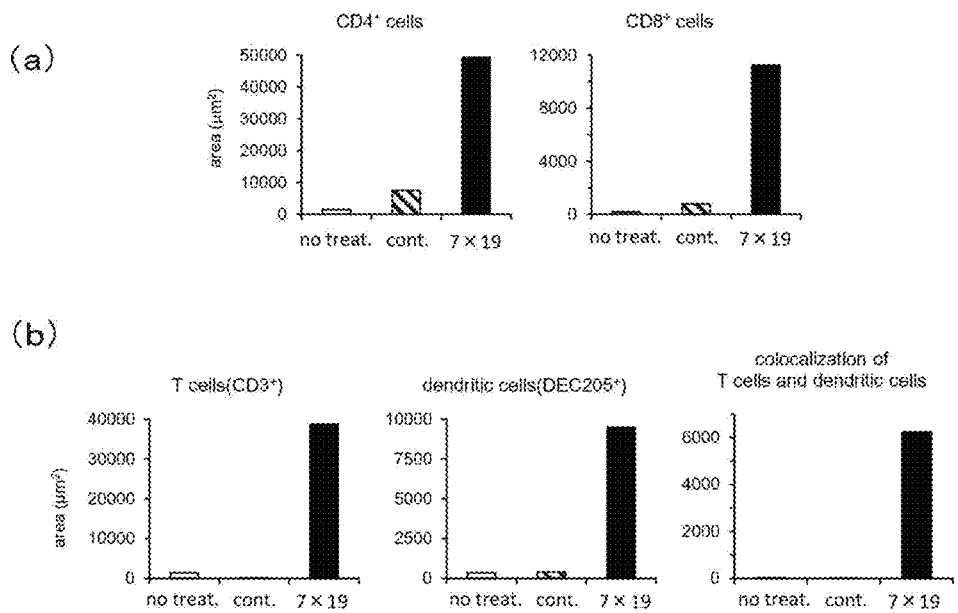
[Figure 28]
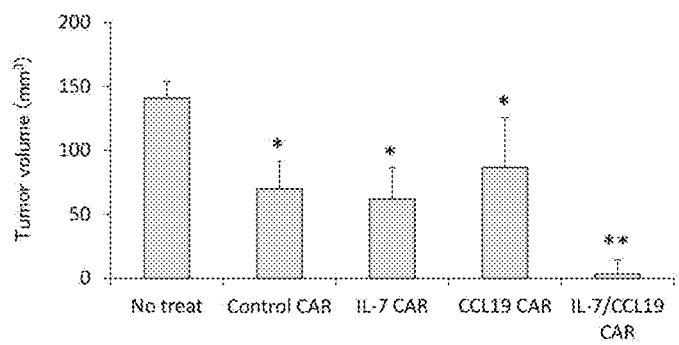
*Statistically significant (p<0.05) compared to no treatment group by student's t-test.
**Statistically significant (p<0.05) compared to other groups by student's t-test.

[Figure 29]
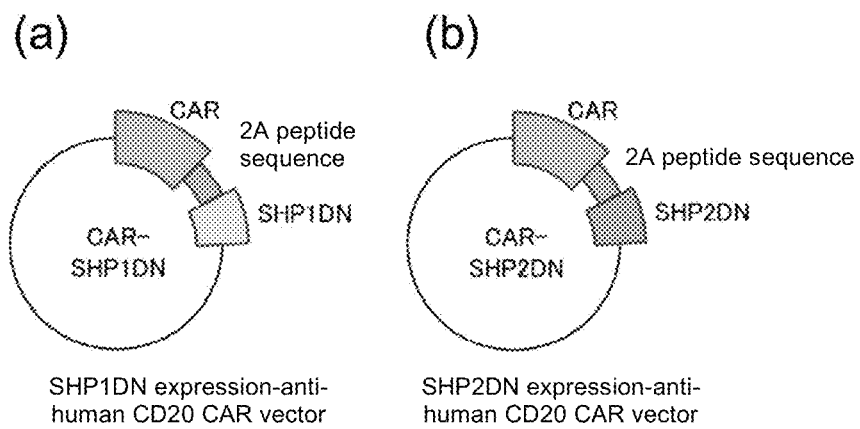

[Figure 30]
(a)
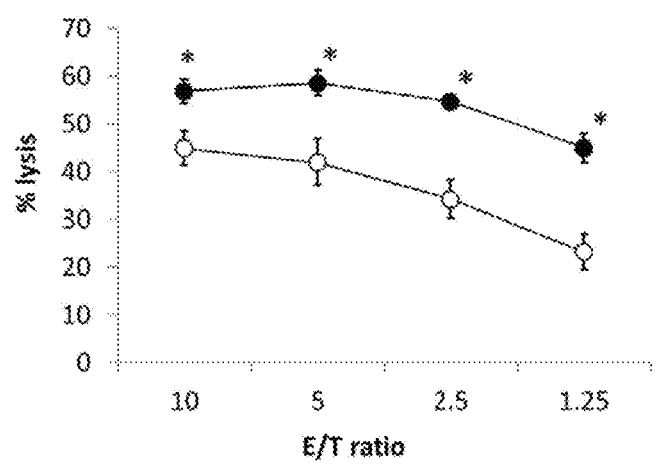
(b)
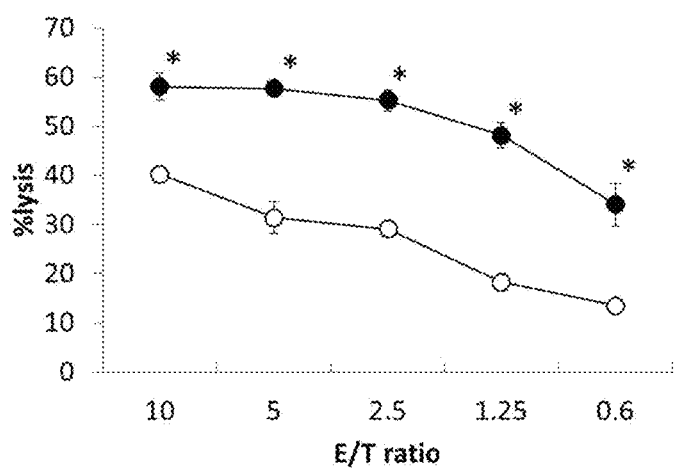
[Figure 31]
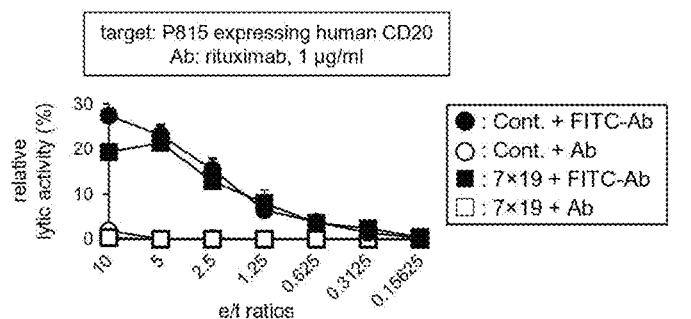

[Figure 32]
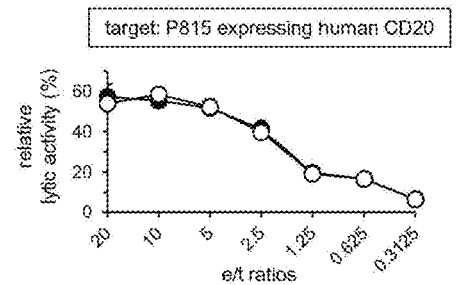
[Figure 33]
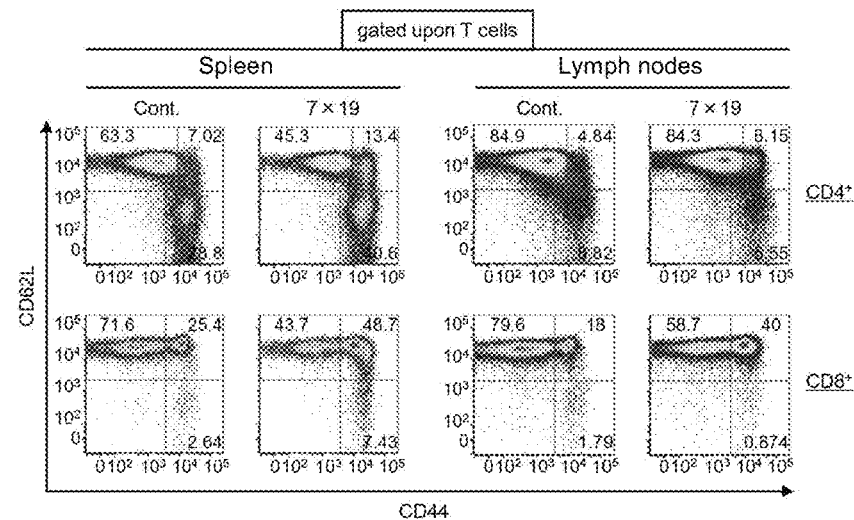
[Figure 34]
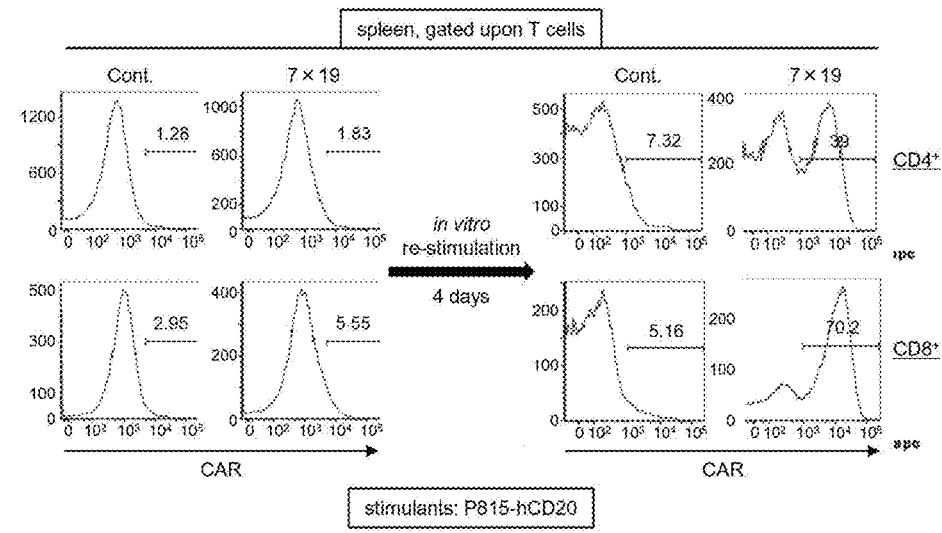

SEQUENCE LISTING

```
<160> NUMBER OF SEQ ID NOS: 12

<210> SEQ ID NO 1
<211> LENGTH: 8
<212> TYPE: PRT
<213> ORGANISM: artificial
<220> FEATURE:
<223> OTHER INFORMATION: 2A peptide cleavage region
<220> FEATURE:
<223> OTHER INFORMATION: Inventor: Tamada, Koji
     Inventor: Sakoda, Yukimi
     Inventor: Adachi, Keishi
<220> FEATURE:
<221> NAME/KEY: MISC_FEATURE
<222> LOCATION: (2)..(2)
<223> OTHER INFORMATION: Val or Ile
<220> FEATURE:
<221> NAME/KEY: MISC_FEATURE
<222> LOCATION: (4)..(4)
<223> OTHER INFORMATION: any amino acid
```

```
<400> SEQUENCE: 1

Asp Xaa Glu Xaa Asn Pro Gly Pro
1               5

<210> SEQ ID NO 2
<211> LENGTH: 25
<212> TYPE: PRT
<213> ORGANISM: artificial
<220> FEATURE:
<223> OTHER INFORMATION: 2Apeptide(F2A)

<400> SEQUENCE: 2

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 3
<211> LENGTH: 177
<212> TYPE: PRT
<213> ORGANISM: artificial
<220> FEATURE:
<223> OTHER INFORMATION: human IL-7

<400> SEQUENCE: 3

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 4
<211> LENGTH: 98
<212> TYPE: PRT
<213> ORGANISM: artificial
<220> FEATURE:
<223> OTHER INFORMATION: human CCL19

<400> SEQUENCE: 4

Met Ala Leu Leu Leu Ala Leu Ser Leu Leu Val Leu Trp Thr Ser Pro
1               5                   10                  15
```

```
Ala Pro Thr Leu Ser Gly Thr Asn Asp Ala Glu Asp Cys Cys Leu Ser
                20                  25                  30

Val Thr Gln Lys Pro Ile Pro Gly Tyr Ile Val Arg Asn Phe His Tyr
            35                  40                  45

Leu Leu Ile Lys Asp Gly Cys Arg Val Pro Ala Val Val Phe Thr Thr
50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser

<210> SEQ ID NO 5
<211> LENGTH: 595
<212> TYPE: PRT
<213> ORGANISM: artificial
<220> FEATURE:
<223> OTHER INFORMATION: human SHP1DN

<400> SEQUENCE: 5

Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
                20                  25                  30

Arg Lys Asn Gln Gly Asp Phe Ser Leu Ser Val Arg Val Gly Asp Gln
            35                  40                  45

Val Thr His Ile Arg Ile Gln Asn Ser Gly Asp Phe Tyr Asp Leu Tyr
        50                  55                  60

Gly Gly Glu Lys Phe Ala Thr Leu Thr Glu Leu Val Glu Tyr Tyr Thr
65                  70                  75                  80

Gln Gln Gln Gly Val Leu Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Glu Asn Lys Gly
            260                 265                 270

Lys Asn Arg Tyr Lys Asn Ile Leu Pro Phe Asp His Ser Arg Val Ile
```

275                 280                 285
Leu Gln Gly Arg Asp Ser Asn Ile Pro Gly Ser Asp Tyr Ile Asn Ala
        290                 295                 300
Asn Tyr Ile Lys Asn Gln Leu Leu Gly Pro Asp Glu Asn Ala Lys Thr
305                 310                 315                 320
Tyr Ile Ala Ser Gln Gly Cys Leu Glu Ala Thr Val Asn Asp Phe Trp
                325                 330                 335
Gln Met Ala Trp Gln Glu Asn Ser Arg Val Ile Val Met Thr Thr Arg
            340                 345                 350
Glu Val Glu Lys Gly Arg Asn Lys Cys Val Pro Tyr Trp Pro Glu Val
        355                 360                 365
Gly Met Gln Arg Ala Tyr Gly Pro Tyr Ser Val Thr Asn Cys Gly Glu
    370                 375                 380
His Asp Thr Thr Glu Tyr Lys Leu Arg Thr Leu Gln Val Ser Pro Leu
385                 390                 395                 400
Asp Asn Gly Asp Leu Ile Arg Glu Ile Trp His Tyr Gln Tyr Leu Ser
                405                 410                 415
Trp Pro Asp His Gly Val Pro Ser Glu Pro Gly Gly Val Leu Ser Phe
            420                 425                 430
Leu Asp Gln Ile Asn Gln Arg Gln Glu Ser Leu Pro His Ala Gly Pro
        435                 440                 445
Ile Ile Val His Ser Ser Ala Gly Ile Gly Arg Thr Gly Thr Ile Ile
    450                 455                 460
Val Ile Asp Met Leu Met Glu Asn Ile Ser Thr Lys Gly Leu Asp Cys
465                 470                 475                 480
Asp Ile Asp Ile Gln Lys Thr Ile Gln Met Val Arg Ala Gln Arg Ser
                485                 490                 495
Gly Met Val Gln Thr Glu Ala Gln Tyr Lys Phe Ile Tyr Val Ala Ile
            500                 505                 510
Ala Gln Phe Ile Glu Thr Thr Lys Lys Lys Leu Glu Val Leu Gln Ser
        515                 520                 525
Gln Lys Gly Gln Glu Ser Glu Tyr Gly Asn Ile Thr Tyr Pro Pro Ala
    530                 535                 540
Met Lys Asn Ala His Ala Lys Ala Ser Arg Thr Ser Ser Lys His Lys
545                 550                 555                 560
Glu Asp Val Tyr Glu Asn Leu His Thr Lys Asn Lys Arg Glu Glu Lys
                565                 570                 575
Val Lys Lys Gln Arg Ser Ala Asp Lys Glu Lys Ser Lys Gly Ser Leu
            580                 585                 590
Lys Arg Lys
        595

<210> SEQ ID NO 6
<211> LENGTH: 593
<212> TYPE: PRT
<213> ORGANISM: artificial
<220> FEATURE:
<223> OTHER INFORMATION: human SHP2DN

<400> SEQUENCE: 6

Met Thr Ser Arg Arg Trp Phe His Pro Asn Ile Thr Gly Val Glu Ala
1               5                   10                  15
Glu Asn Leu Leu Leu Thr Arg Gly Val Asp Gly Ser Phe Leu Ala Arg
            20                  25                  30
Pro Ser Lys Ser Asn Pro Gly Asp Phe Thr Leu Ser Val Arg Arg Asn

```
              35                  40                  45
Gly Ala Val Thr His Ile Lys Ile Gln Asn Thr Gly Asp Tyr Tyr Asp
 50                  55                  60

Leu Tyr Gly Gly Glu Lys Phe Ala Thr Leu Ala Glu Leu Val Gln Tyr
 65                  70                  75                  80

Tyr Met Glu His His Gly Gln Leu Lys Glu Lys Asn Gly Asp Val Ile
                 85                  90                  95

Glu Leu Lys Tyr Pro Leu Asn Cys Ala Asp Pro Thr Ser Glu Arg Trp
                100                 105                 110

Phe His Gly His Leu Ser Gly Lys Glu Ala Glu Lys Leu Leu Thr Glu
                115                 120                 125

Lys Gly Lys His Gly Ser Phe Leu Val Arg Glu Ser Gln Ser His Pro
            130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
                180                 185                 190

Leu Val Glu His Tyr Lys Lys Asn Pro Met Val Glu Thr Leu Gly Thr
                195                 200                 205

Val Leu Gln Leu Lys Gln Pro Leu Asn Thr Thr Arg Ile Asn Ala Ala
210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
                260                 265                 270

Asn Lys Asn Lys Asn Arg Tyr Lys Asn Ile Leu Pro Phe Asp His Thr
            275                 280                 285

Arg Val Val Leu His Asp Gly Asp Pro Asn Glu Pro Val Ser Asp Tyr
290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
                340                 345                 350

Ile Val Met Thr Thr Lys Glu Val Glu Arg Gly Lys Ser Lys Cys Val
            355                 360                 365

Lys Tyr Trp Pro Asp Glu Tyr Ala Leu Lys Glu Tyr Gly Val Met Arg
            370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415

Gln Tyr His Phe Arg Thr Trp Pro Asp His Gly Val Pro Ser Asp Pro
                420                 425                 430

Gly Gly Val Leu Asp Phe Leu Glu Glu Val His His Lys Gln Glu Ser
            435                 440                 445

Ile Met Asp Ala Gly Pro Val Val His Ser Ser Ala Gly Ile Gly
            450                 455                 460
```

```
Arg Thr Gly Thr Phe Ile Val Ile Asp Ile Leu Ile Asp Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
                500                 505                 510

Phe Ile Tyr Met Ala Val Gln His Tyr Ile Glu Thr Leu Gln Arg Arg
            515                 520                 525

Ile Glu Glu Gln Lys Ser Lys Arg Lys Gly His Glu Tyr Thr Asn
530                 535                 540

Ile Lys Tyr Ser Leu Ala Asp Gln Thr Ser Gly Asp Gln Ser Pro Leu
545                 550                 555                 560

Pro Pro Cys Thr Pro Thr Pro Pro Cys Ala Glu Met Arg Glu Asp Ser
                565                 570                 575

Ala Arg Val Tyr Glu Asn Val Gly Leu Met Gln Gln Gln Lys Ser Phe
            580                 585                 590

Arg
```

```
<210> SEQ ID NO 7
<211> LENGTH: 1674
<212> TYPE: DNA
<213> ORGANISM: artificial
<220> FEATURE:
<223> OTHER INFORMATION: anti-FITC CAR

<400> SEQUENCE: 7
atggagttgc ctgttaggtt gttggtgctg atgttctgga ttcctgcttc cagcagtgat        60
gtcgtgatga cccaaactcc actctccctg cctgtcagtc ttggagatca agcctccatc       120
tcttgcagat ctagtcagag ccttgtacac agtaatggaa acacctattt acgttggtac       180
ctgcagaagc caggccagtc tccaaaggtc ctgatctaca agtttccaa ccgattttct        240 ggggtcccag acaggttcag tggcagtgga tcaggacag atttcacact caagatcagc        300
agagtggagg ctgaggatct ggagttttat ttctgctctc aaagtacaca tgttccgtgg       360
acgttcggtg aggcaccaa gctggaaatc aaaagtagtg ctgatgatgc taagaaggat        420
gctgctaaga aggatgatgc taagaaggat gatgctaaga aggatggtga ggtgaagctg       480
gatgagactg gaggaggctt ggtgcaacct gggaggccca tgaaactctc ctgtgttgcc       540
tctggattca ctttagtga ctactggatg aactgggtcc gccagtctcc agagaaagga       600
ctggagtggg tagcacaaat tagaaacaaa cctataatt atgaaacata ttattcagat       660
tctgtgaaag gcagattcac catctcaaga gatgattcca aaagtagtgt ctacctgcaa       720
atgaacaact taagagttga agacatgggt atcattact gtacgggttc ttactatggt       780
atggactact gggtcaagg aacctcagtc accgtctccg cggccgcagt cgtgccagtc       840
cttcagaaag tgaactctac tactaccaag ccagtgctgc gaactccctc acctgtgcac       900
cctaccggga catctcagcc cagagaacca gaagattgtc ggccccgtgg ctcagtgaag       960
gggaccggat tggacttcgc ctgtgatatt tacatctggg cacccttggc cggaatctgc      1020
gtggcccctc tgctgtcctt gatcatcact ctcatctgct accacaggag ccgaaatagt      1080
agaaggaaca gactccttca agtgactac atgaacatga ctccccggag gcctgggctc      1140
actcgaaagc cttaccagcc ctacgcccct gccagagact tgcagcgta ccgccccaaa      1200 tggatcagga aaaaattccc ccacatattc aagcaaccat taagaagac cactggagca      1260
```

| gctcaagagg aagatgcttg tagctgccga tgtccacagg aagaagaagg aggaggagga | 1320 |
| ggctatgagc tgagagcaaa attcagcagg agtgcagaga ctgctgccaa cctgcaggac | 1380 |
| cccaaccagc tctacaatga gctcaatcta gggcgaagag aggaatatga cgtcttggag | 1440 |
| aagaagcggg ctcgggatcc agagatggga ggcaaacagc agaggaggag gaaccccccag | 1500 |
| gaaggcgtat acaatgcact gcagaaagac aagatggcag aagcctacag tgagatcggc | 1560 |
| acaaaaggcg agaggcggag aggcaagggg cacgatggcc tttaccaggg tctcagcact | 1620 |
| gccaccaagg acacctatga tgccctgcat atgcagaccc tggcccctcg ctaa | 1674 |

<210> SEQ ID NO 8
<211> LENGTH: 146
<212> TYPE: DNA
<213> ORGANISM: artificial
<220> FEATURE:
<223> OTHER INFORMATION: F2A-MCS

<400> SEQUENCE: 8

| ggaagcggag tgaaacagac tttgaatttt gaccttctca agttggcggg agacgtggag | 60 |
| tccaaccctg gaccatgcat aaaaagctta aaccagttaa ctggaaaacg cgtaaagtcg | 120 |
| acaaaggcca aaaaggccaa cgtacg | 146 |

<210> SEQ ID NO 9
<211> LENGTH: 864
<212> TYPE: DNA
<213> ORGANISM: artificial
<220> FEATURE:
<223> OTHER INFORMATION: mouseIL-7-F2A-mouseCCL19

<400> SEQUENCE: 9

| atgttccatg tttcttttag atatatcttt ggaattcctc cactgatcct tgttctgctg | 60 |
| cctgtcacat catctgagtg ccacattaaa gacaaagaag gtaaagcata tgagagtgta | 120 |
| ctgatgatca gcatcgatga attggacaaa atgacaggaa ctgatagtaa ttgcccgaat | 180 |
| aatgaaccaa actttttag aaaacatgta tgtgatgata caaggaagc tgctttttcta | 240 |
| aatcgtgctg ctcgcaagtt gaagcaattt cttaaaatga atatcagtga agaattcaat | 300 |
| gtccacttac taacagtatc acaaggcaca caaacactgg tgaactgcac aagtaaggaa | 360 |
| gaaaaaacg taaggaaca gaaaaagaat gacgcatgtt tcctaaagag actactgaga | 420 |
| gaaataaaaa cttgttggaa taaattttg aagggcagta taggaagcgg agtgaaacag | 480 |
| actttgaatt ttgaccttct caagttggcg ggagacgtgg agtccaaccc tggacctatg | 540 |
| gccccccgtg tgacccccact cctggccttc agcctgctgg ttctctggac cttcccagcc | 600 |
| ccaactctgg ggggtgctaa tgatgcgaa gactgctgcc tgtctgtgac ccagcgcccc | 660 |
| atccctggga acatcgtgaa agccttccgc taccttctta atgaagatgg ctgcagggtg | 720 |
| cctgctgttg tgttcaccac actaagggc tatcagctct gtgcacctcc agaccagccc | 780 |
| tgggtggatc gcatcatccg aagactgaag aagtcttctg ccaagaacaa aggcaacagc | 840 |
| accagaagga gccctgtgtc ttga | 864 |

<210> SEQ ID NO 10
<211> LENGTH: 783
<212> TYPE: DNA
<213> ORGANISM: artificial
<220> FEATURE:
<223> OTHER INFORMATION: anti-humanCD20 scFv

<400> SEQUENCE: 10

```
atggactgga cctggcggat cctgttcctg gtggctgctg ctacaggcgc ccacagccag    60
atcgtgctgt ctcagtctcc cgccatcctg tctgctagcc ctggcgagaa agtgaccatg   120
acctgcagag ccagcagcag cgtgtcctac atccactggt tccagcagaa gcccggcagc   180
agccccaagc cttggatcta cgccacaagc aacctggcct ctggcgtgcc agtgcggttt   240
agcggctctg gctctggcac cagctacagc ctgaccatca gcagagtgga agccgaggac   300
gccgccacct actactgtca gcagtggacc agcaaccccc ccacattcgg cggaggcacc   360
aagctggaaa tcaagggcgg aggcggatct ggcggcggag atctgggggg aggcggctct   420
caggtgcagc tgcagcagcc tggcgctgag ctcgtgaaac tggcgcctc cgtgaagatg   480
agctgcaagg ccagcggcta caccttcaca agctacaaca tgcactgggt caagcagacc   540
cctggcagag gcctggaatg gatcggcgct atctaccccg gcaacggcga cacctcctac   600
aaccagaagt tcaagggcaa ggccaccctg accgccgaca gagcagcag cacagcctac   660
atgcagctgt cctccctgac cagcgaggac agcgccgtgt actactgcgc cagatctacc   720
tactacggcg gcgactggta cttcaacgtg tggggcgctg gcaccaccgt gaccgtgtct   780
gct                                                                 783
```

<210> SEQ ID NO 11
<211> LENGTH: 1788
<212> TYPE: DNA
<213> ORGANISM: artificial
<220> FEATURE:
<223> OTHER INFORMATION: mouse SHP1DN

<400> SEQUENCE: 11

```
atggtgaggt ggtttcaccg ggacctcagc gggcctgatg cagagaccct gctgaagggc    60
cggggagtcc ctgggagctt cctggctcgg cccagccgca agaaccaggg tgacttctcc   120
ctctcagtca gggtggatga tcaggtgact catattcgga tccagaactc aggggacttc   180
tatgacctgt acggagggga gaagtttgcg acgctgacag agctggtcga gtattacacg   240
cagcagcagg gcatcctgca ggaccgagat ggcaccatca tccaccttaa gtacccactg   300
aactgctcgg accccaccag tgagaggtgg taccacggcc acatatctgg agggcaggcg   360
gagtcactgc tgcaggccaa gggcgagccc tggacatttc ttgtgcgtga gagtctcagc   420
caacctggtg attttgtgct ctctgtgctc aatgaccagc caaggctggg cccaggttcc   480
ccgctcaggg tcactcatat caaggttatg tgtgagggtg gacgctatac tgtgggtggc   540
tcagagacgt ttgacagcct cacagacctg gtggagcact tcaagaagac agggattgag   600
gaggcctcgg gtgccttgt ctacctgcgg cagccttact acgctactcg ggtaaacgca   660
gctgacattg agaatcgggt cttggaactg aacaagaagc aggagtcgga ggacacagcc   720
aaggctggct tctgggagga gtttgagagt ctacaaaagc aggaggtaaa gaatctacac   780
caacgtctgg aagggcagcg gccagagaac aagagcaaga accgctacaa gaacattctt   840
ccctttgacc acagccgagt gatcctgcag ggacgtgaca gtaacatccc aggctctgac   900
tacatcaatg ccaactacgt gaagaaccag ctgctaggtc agatgagaa ctctaagacc   960
tacatcgcca gccagggctg tctggatgcc acagtcaatg acttctggca gatggcttgg  1020
caggagaaca ctcgtgtcat cgtcatgact accagagagg tggagaaagg ccggaacaaa  1080
tgtgtcccat actggcccga ggtgggcact cagcgtgtct atggtctcta ctctgtgacc  1140
aacagtaggg agcatgacac agcagaatac aaactgcgaa cattacagat ctccccacta  1200
```

-continued

| | |
|---|---|
| gacaatgggg acctggttcg ggagatatgg cactaccagt acctgagctg gcctgaccat | 1260 |
| ggggttccca gtgagcctgg gggtgtcctc agctttctgg atcagatcaa ccagcgacag | 1320 |
| gaaagtttgc ctcatgcagg gcccatcatt gtgcattcca gcgctggcat cggccgcacg | 1380 |
| ggcaccatca tcgtcattga tatgcttatg gaaagcatct ccaccaaggg gctagactgt | 1440 |
| gacattgata tccagaagac catccagatg gtacgagcac agcgctccgg catggtgcag | 1500 |
| accgaggccc agtacaagtt tatttacgtg gccattgccc agttcatcga aacgaccaag | 1560 |
| aagaaactgg agatcataca atcccagaag ggccaggagt cggagtatgg aatatcacg | 1620 |
| taccctcccg ctgtgaggag tgcccacgcc aaagcctcgc gtacttcctc caagcacaag | 1680 |
| gaggaggtgt acgaaaacgt gcatagcaag agcaagaagg aagagaaagt aaagaagcag | 1740 |
| cggtcggcag acaaggagaa gaacaaaggt tctctcaaga ggaagtga | 1788 |

<210> SEQ ID NO 12
<211> LENGTH: 1782
<212> TYPE: DNA
<213> ORGANISM: artificial
<220> FEATURE:
<223> OTHER INFORMATION: mouse SHP2DN

<400> SEQUENCE: 12

| | |
|---|---|
| atgacatcgc ggagatggtt tcaccccaac atcactggtg tggaggcaga gaatctcctg | 60 |
| ctgaccagag gagtcgatgg cagttttta gcaaggccca gtaagagtaa ccctggagac | 120 |
| ttcactctgt ctgttagaag aaatggagct gttacccaca tcaagattca gaacactggg | 180 |
| gactactatg acctctatgg tggggagaag tttgccactt ggctgaact ggttcagtat | 240 |
| tacatggaac accatgggca gctgaaagag aagaatggag atgttatcga gctcaagtac | 300 |
| ccgctgaact gtgcagaccc tacctctgaa aggtggttcc atggtcactt gtctggaaaa | 360 |
| gaagcagaga gctgctgac ggagaagggc aagcatggca gcttcctcgt tcgagagagc | 420 |
| cagagccacc ccggagactt cgttctctcc gtgcgcactg tgacgacaa aggggagagc | 480 |
| aacgacggca agtccaaagt gacccacgtc atgatccgct gtcaggagct gaaatacgac | 540 |
| gttggtgggg gagagcgctt tgactctctg acagacctgg tggagcatta caagaagaac | 600 |
| cccatggtgg agacgctggg cacagtcctg cagctcaagc agcccctcaa cacaactcgt | 660 |
| atcaatgctg ctgaaattga agccgggtt cgagagttaa gcaagctggc tgagaccaca | 720 |
| gataaagtca agcagggctt tgggaagag tttgagacgc tccagcaaca ggaatgcaaa | 780 |
| cttctctata gccgaaaaga aggacagaga caagaaaata aaaacaaaaa cagatacaaa | 840 |
| aacatcctgc cctttgatca taccagggtc gttctgcatg atgggatcc caatgagcct | 900 |
| gtttctgatt acattaatgc aaacatcatc atgcctgagt ttgagaccaa gtgcaacaat | 960 |
| tccaaaccca aaagagtta cattgccact caaggctgcc tgcagaacac ggtgaatgac | 1020 |
| ttctggcgga tggtgttcca ggagaactct cgagtcattg tcatgaccac aaaggaagtg | 1080 |
| gagagaggga agagcaaatg tgtcaagtac tggcctgatg agtatgcgct caaagaatac | 1140 |
| ggggtcatgc gtgttaggaa cgtcaaagaa agtgccgccc atgactacac tttacgagag | 1200 |
| ctcaaactct ctaaggtcgg acaaggaaac acagagagaa ccgtctggca gtaccacttt | 1260 |
| cggacctggc cagaccatgg cgtgcctagt gaccctggag gtgtgctgga cttcctggag | 1320 |
| gaggtccacc acaagcagga gagcatcgtg gatgcaggcc ctgtcgtggt tcactccagc | 1380 |
| gctgggattg gccggacagg aaccttcatt gtgattgaca tccttattga catcattcga | 1440 |
| gagaaaggtg tggactgtga catcgacgtt cctaaaacca ttcagatggt gcggtcccag | 1500 |

```
aggtcgggga tggtccagac agaagcacag taccggttta tctacatggc tgtccagcac    1560
tacatagaga cgctgcagcg ccggatcgag gaggagcaga aaagcaaaag aaaaggacat    1620
gaatatacca atattaagta ttccttggtg gaccagacaa gtggtgatca gagtcccctg    1680
ccaccctgca ccccaacgcc accctgtgca gaaatgaggg aggacagcgc ccgagtctat    1740
gagaacgtgg gcctcatgca gcagcagagg agtttcagat ga                      1782
```

CAR EXPRESSION VECTOR AND CAR-EXPRESSING T CELLS

TECHNICAL FIELD

The present invention relates to a CAR expression vector, a CAR-expressing T cell introduced with the CAR expression vector, and an anticancer agent comprising the CAR-expressing T cell.

BACKGROUND ART

A chimeric antigen receptor (hereinafter, also referred to as "CAR") is an artificial chimeric protein in which a single chain antibody that recognizes a cell surface antigen on a cancer cell is fused with a signal transduction region that induces the activation of a T cell. As shown in FIG. 1, the transfer of a gene encoding CAR to a non-tumor-reactive normal peripheral blood T cell (peripheral blood T lymphocyte) enables the large-scale preparation of a CAR-expressing T cell (hereinafter, also simply referred to as "CAR-T cell") that are capable of expressing CAR. The CAR-T cell is tumor-reactive and can cause damage to a cancer cell without depending on interaction with a major histocompatibility complex (MHC).

Cancer immunotherapy by the administration of the CAR-T cells, more specifically, therapy which involves collecting T cells from a patient, transferring a gene encoding CAR to the T cells, and transferring the T cells again to the patient (see non-patent document 1) is currently under clinical trial around the world and has yielded results that indicate effectiveness for, for example, malignant tumor in the hematopoietic organ, such as leukemia or lymphoma.

In recent years, research has been made on various CAR-T cells. There have been proposed, for example, a pharmaceutical composition comprising modified autologous human T cells comprising a nucleic acid encoding CAR consisting of a CD19 antigen-binding region, a transmembrane region, a 4-1BB costimulatory signal region, and a CD3ζ signal region (see patent document 1), one or more therapeutically effective anti-tag chimeric antigen receptor (AT-CAR)-expressing T cell populations which are administered to a subject concurrently with or separately from a formulation of one or more tagged proteins binding to cancer cells, wherein the AT-CAR-expressing T cell populations bind to the tagged proteins and induce cancer cell death (see patent document 2), cells comprising a nucleic acid encoding a chimeric antigen receptor comprising an antigen-binding domain of human antibody 139, an extracellular hinge domain, a transmembrane domain, and an intracellular T cell signal transduction domain (see patent document 3), cells comprising a nucleic acid sequence encoding a chimeric antigen receptor, wherein the chimeric antigen receptor comprises a CD3ζ signal transduction domain comprising an antigen-binding domain, a transmembrane domain, a costimulatory signal transduction region, and the amino acid sequence of SEQ ID NO:24 (see patent document 4), genetically engineered CD19-specific T cells which express and retain a CD19-specific chimeric receptor on their cell surface membranes, wherein the chimeric receptor consists of an intracellular signaling domain for immunocyte effector functions, at least one transmembrane domain, and at least one extracellular domain, and the extracellular domain comprises a CD19-specific receptor (see patent document 5), and chimeric antigen receptor-expressing cells harboring a nucleic acid encoding a chimeric antigen receptor comprising, as an intracellular domain, an intracellular domain of a glucocorticoid-induced tumor necrosis factor receptor (GITR) (see patent document 6).

However, none of the previous techniques have solved the problem of low survival efficiency of CAR-T cells in vivo or insufficient activation of endogenous T cells induced by CAR-T cells or insufficient local accumulation thereof to tumor, or the problems of immunosuppressive signals mediated by the PD-L1/PD-1 pathway which is the tumor immune escape mechanism of cancer cells, and the inhibition of the activity of CAR-T cells by immunosuppressive factors such as TGF-β or IL-10 secreted in a cancer microenvironment. Therefore, there exist cancer types or cases on which no sufficient therapeutic effect is confirmed. Thus, it has been desired to prepare more effective CAR-T cells, and an expression vector for the preparation of the CAR-T cells.

PRIOR ART DOCUMENTS

Patent Documents

Patent Document 1: U.S. Patent Application Publication No. 2014/0106449
Patent Document 2: Japanese unexamined Patent Application Publication (Translation of PCT Application) No. 2014-504294
Patent Document 3: Japanese unexamined Patent Application Publication (Translation of PCT Application) No. 2014-516510
Patent Document 4: Japanese unexamined Patent Application Publication (Translation of PCT Application) No. 2014-507118
Patent Document 5: Japanese unexamined Patent Application Publication No. 2011-004749
Patent Document 6: International Publication No. WO 2013/051718

Non-Patent Documents

Non-patent Document 1: Yozo Nakazawa, The Shinshu Medical Journal, 61 (4): 197-203 (2013)

SUMMARY OF THE INVENTION

Object to be Solved by the Invention

Conventional CAR-T cells have been designed to enhance the ability to activate T cells by containing CD28, 4-1BB, CD3ζ, or the like in the signal transduction region of CAR. However, the conventional CAR-T cells do not sufficiently potentiate the immunity-inducing effect of the CAR-T cells on endogenous T cells or resistance to the immunosuppressive mechanism of a tumor microenvironment. Such CAR-T cells have not yet attained a therapeutic effect on solid cancer. Accordingly, an object of the present invention is to provide CAR-T cells that coexpress CAR and a T cell immune function-enhancing factor and have a high immunity-inducing effect and antitumor activity, and to provide a CAR expression vector for the preparation of the CAR-T cells.

Means to Solve the Object

The inventors have attempted to improve CAR-T cells for the purpose of achieving a better immunity-inducing effect or antitumor activity in cancer immunotherapy using CAR-T cells. During the course thereof, the inventors have focused on cytokines, chemokines, and signal regulatory proteins which are factors enhancing the immune functions of T cells, and constructed a vector for the coexpression of CAR and the factors enhancing the immune functions of T cells. As a result of transferring this expression vector to T cells, the inventors have found that CAR-T cells superior in immunity-inducing effect and antitumor activity to the conventional CAR-T cells can be prepared, and thereby completed the present invention.

Specifically, the present invention is as disclosed below.
(1) A CAR expression vector comprising a nucleic acid encoding a chimeric antigen receptor (CAR) and a nucleic acid encoding a T cell immune function-enhancing factor, wherein the nucleic acid encoding an immune function-enhancing factor is a nucleic acid encoding interleukin-7 and a nucleic acid encoding CCL19, a nucleic acid encoding a dominant negative mutant of SHP-1, or a nucleic acid encoding a dominant negative mutant of SHP-2.
(2) The CAR expression vector according to (1), wherein the nucleic acid encoding an immune function-enhancing factor is a nucleic acid encoding interleukin-7 and a nucleic acid encoding CCL19.
(3) The CAR expression vector according to (2), wherein the nucleic acid encoding CAR and the nucleic acid encoding a T cell immune function-enhancing factor are linked via a sequence encoding a self-cleaving peptide.
(4) The CAR expression vector according to (2) or (3), wherein the nucleic acid encoding interleukin-7 and the nucleic acid encoding CCL19 are linked via a sequence encoding a self-cleaving peptide.
(5) The CAR expression vector according to any one of (1) to (4), wherein the nucleic acid encoding CAR contains a nucleic acid encoding a polypeptide of a single chain antibody that recognizes FITC or CD20.
(6) The CAR expression vector according to any one of (1) to (5), wherein the nucleic acid encoding CAR contains a nucleic acid encoding a polypeptide of a CD8 transmembrane region.
(7) The CAR expression vector according to any one of (1) to (6), wherein the nucleic acid encoding CAR contains nucleic acids encoding polypeptides of a CD28 intracellular region, a 4-1BB intracellular region, and a CD3ζ intracellular region.
(8) A CAR-expressing T cell introduced with the following vector (a) or (b):
(a) the CAR expression vector according to any one of (1) to (7);
(b) a CAR expression vector containing a nucleic acid encoding CAR and a nucleic acid encoding interleukin-7, and a CAR expression vector containing a nucleic acid encoding CAR and a nucleic acid encoding CCL19.
(9) An anticancer agent comprising the CAR-expressing T cell according to (8) and a pharmaceutically acceptable additive.

Effect of the Invention

Use of the CAR expression vector of the present invention enables the preparation of CAR-T cell having all of viability, the ability to accumulate lymphocytes, and cytotoxic activity against tumor cells, and CAR-T cell having resistance to immunosuppression in a cancer microenvironment. Immunotherapy for cancer patients using the CAR-T cell is expected to produce a strong therapeutic effect on cancer and can serve as cancer immunotherapy effective even for intractable or progressive cancer.

BRIEF DESCRIPTION OF DRAWINGS

FIG. 1 is a diagram showing the structure of CAR and the basic system of cancer immunotherapy using CAR-T cells.

FIG. 2 is a diagram showing a vector for the expression of CAR, interleukin-7 (IL-7), and CCL19.

FIG. 3 is a diagram showing results-1 of confirming the expression level of CAR in anti-FITC CAR-IL-7/CCL19-expressing T cells by flow cytometry. The left graph depicts an unstained CAR sample, and the right graph depicts a stained CAR sample.

FIG. 4 is a diagram showing results-2 of confirming the expression level of CAR in anti-FITC CAR-IL-7/CCL19-expressing T cells by flow cytometry.

FIG. 5 is a diagram showing results of confirming the expression level of CAR in anti-human CD20 CAR-IL-7/CCL19-expressing T cells by flow cytometry.

FIG. 6 is a diagram showing results-1 of measuring the concentrations of IL-7 and CCL19 in the cell supernatant of anti-FITC CAR-IL-7/CCL19-expressing T cells by ELISA.

FIG. 7 is a diagram showing results-2 of measuring the concentrations of IL-7 and CCL19 in the cell supernatant of anti-FITC CAR-IL-7/CCL19-expressing T cells by ELISA.

FIG. 8 is a diagram showing results of measuring the concentrations of IL-7 and CCL19 in the cell supernatant of anti-human CD20 CAR-IL-7/CCL19-expressing T cells by ELISA.

FIG. 9 is a diagram showing the cell number of anti-FITC CAR-IL-7/CCL19-expressing T cells stimulated and cultured for 3 days, 5 days, or 7 days.

FIG. 10 is a diagram showing the survival rate of the anti-FITC CAR-IL-7/CCL19-expressing T cells stimulated and cultured for 3 days, 5 days, or 7 days.

FIG. 11 is a diagram showing the cell number of anti-human CD20 CAR-IL-7/CCL19-expressing T cells stimulated and cultured for 5 days.

FIG. 12 is a diagram showing results-1 of a T cell migration test using anti-FITC CAR-IL-7/CCL19-expressing T cells.

FIG. 13 is a diagram showing results-2 of the T cell migration test using anti-FITC CAR-IL-7/CCL19-expressing T cells.

FIG. 14 is a diagram showing results of a dendritic cell migration test using anti-FITC CAR-IL-7/CCL19-expressing T cells.

FIG. 15 is a diagram showing results of a T cell migration test using anti-human CD20 CAR-IL-7/CCL19-expressing T cells.

FIG. 16 is a diagram showing results of examining the T cell proliferative potential of anti-FITC CAR-IL-7/CCL19-expressing T cells (day 5 post-stimulation).

FIG. 17 is a diagram showing results of examining the T cell proliferative potential of anti-FITC CAR-IL-7/CCL19-expressing T cells (days 3 and 7 post-stimulation).

FIG. 18 is a diagram showing results of examining the expression of CD127 in anti-FITC CAR-IL-7/CCL19-expressing T cells.

FIG. 19 is a diagram showing results of examining the expression of CCR7 in anti-FITC CAR-IL-7/CCL19-expressing T cells.

FIG. 20 is a diagram showing results of examining change in tumor volume when anti-human CD20 CAR-IL-7/CCL19-expressing T cells were administered to cancer-bearing mice.

FIG. 21 is a diagram showing results of examining a mouse survival rate when anti-human CD20 CAR-IL-7/CCL19-expressing T cells were administered to cancer-bearing mice.

FIG. 22 is a diagram showing results of examining a mouse survival rate when anti-human CD20 CAR-IL-7/CCL19-expressing T cells were administered to mice after subcutaneous inoculation of P815-hCD20 and subsequent administration of cyclophosphamide.

FIG. 23 is a diagram showing results of examining a mouse tumor volume when anti-human CD20 CAR-IL-7/CCL19-expressing T cells were administered to mice after subcutaneous inoculation of P815-hCD20 and subsequent administration of cyclophosphamide.

FIG. 24 is a diagram showing 1/10 of numerical values on the ordinate of the graph of CPA+7×19 in FIG. 23.

FIG. 25 is a diagram showing results of observing tumor tissues by H&E staining when anti-human CD20 CAR-IL-7/CCL19-expressing T cells were administered to mice after subcutaneous inoculation of P815-hCD20.

FIG. 26 is a diagram showing results of immunohistochemically analyzing tumor tissues when anti-human CD20 CAR-IL-7/CCL19-expressing T cells were administered to mice after subcutaneous inoculation of P815-hCD20.

FIG. 27 is a diagram showing results of quantifying the positive region labeled by fluorescent staining in FIG. 26.

FIG. 28 is a diagram showing results of examining a tumor volume when anti-human CD20 CAR-IL-7-expressing T cells, anti-human CD20 CAR-CCL19-expressing T cells, or anti-human CD20 CAR-IL-7/CCL19-expressing T cells were administered to mice after subcutaneous inoculation of P815-hCD20.

FIG. 29(a) is a diagram showing a vector for the expression of CAR and a dominant negative mutant of SHPT (Src homology region 2 domain-containing phosphatase-1). FIG. 29(b) is a diagram showing a vector for the expression of CAR and a dominant negative mutant of SHP2 (Src homology region 2 domain-containing phosphatase-2).

FIG. 30(a) is a diagram showing results of a cytotoxic activity test using anti-human CD20 CAR-SHP1DN-expressing T cells. FIG. 30(b) is a diagram showing a cytotoxic activity test using anti-human CD20 CAR-SHP2DN-expressing T cells.

FIG. 31 is a diagram showing results of examining cytotoxic activity against tumor cells by mixing P815-hCD20 in the presence of anti-FITC CAR-IL-7/CCL19-expressing T cells and FITC-bound rituximab.

FIG. 32 is a diagram showing results of examining cytotoxic activity against tumor cells by mixing P815-hCD20 with anti-human CD20 CAR-IL-7/CCL19-expressing T cells.

FIG. 33 is a diagram showing results of analyzing CD4, CD8, CD44, and CD62L for the surface phenotypes of leukocytes by flow cytometry when anti-human CD20 CAR-IL-7/CCL19-expressing T cells were administered to mice after subcutaneous inoculation of P815-hCD20.

FIG. 34 is a diagram showing results of examining the proliferation of T cells by flow cytometry when spleen leukocytes were stimulated by culture for 4 days with P815-hCD20 treated with mitomycin C.

MODE OF CARRYING OUT THE INVENTION

The CAR expression vector of the present invention is not particularly limited as long as the CAR expression vector comprises a nucleic acid encoding a chimeric antigen receptor (CAR) and a nucleic acid encoding a T cell immune function-enhancing factor, wherein the nucleic acid encoding an immune function-enhancing factor is a nucleic acid encoding interleukin-7 and a nucleic acid encoding CCL19, a nucleic acid encoding a dominant negative mutant of SHP-1, or a nucleic acid encoding a dominant negative mutant of SHP-2. The chimeric antigen receptor means an artificial chimeric protein in which a single chain antibody that recognizes a cell surface antigen on a cancer cell is fused with a signal transduction region that induces the activation of a T cell, via a transmembrane region.

In the present invention, the nucleic acid encoding CAR is not particularly limited as long as the nucleic acid encodes a polypeptide constituting CAR. The nucleic acid encoding CAR comprises nucleic acids encoding polypeptides of a single chain antibody that recognizes a cell surface antigen on a cancer cell, a transmembrane region, and a signal transduction region that induces the activation of a T cell.

The single chain antibody in CAR consists of a light chain variable region and a heavy chain variable region (scFv) derived from the antigen-binding site of a monoclonal antibody. Examples thereof can include an oligopeptide or a polypeptide in which a linker peptide is positioned between the light chain variable region and the heavy chain variable region.

The cell surface antigen on a cancer cell that is recognized by the single chain antibody can be a biological molecule specifically expressed on a cancer cell and a progenitor cell thereof, a biological molecule found to be newly expressed due to the malignant transformation of a cell, or a biological molecule whose expression level is increased in a cancer cell compared with a normal cell. Examples thereof can include CD20, EGFR, FITC, CD19, CD22, CD33, PSMA, GD2, EGFR variants, ROR1, c-Met, HER2, CEA, mesothelin, GM2, CD7, CD10, CD30, CD34, CD38, CD41, CD44, CD74, CD123 CD133, CD171, MUC16, MUC1, CS1 (CD319), IL-13Ra2, BCMA, Lewis Y, IgG kappa chain, folate receptor-alpha, PSCA, and EpCAM.

The T cell activation signal transduction region is a region that is capable of intracellularly transducing signals when the single chain antibody recognizes the cell surface antigen on a cancer cell. The T cell activation signal transduction region preferably comprises at least one or more polypeptides selected from polypeptides of CD28, 4-1BB (CD137), GITR, CD27, OX40, HVEM, CD3ζ, and Fc receptor-associated γ chain intracellular regions and more preferably comprises polypeptides of three intracellular regions of CD28, 4-1BB, and CD3ζ.

These polypeptides of the intracellular regions may be linked via an oligopeptide linker or a polypeptide linker consisting of 2 to 10 amino acids. Examples of such a linker sequence can include glycine-serine consecutive sequences.

Examples of the transmembrane region according to the present invention can include polypeptides of transmembrane regions derived from CD8, T cell receptor α and β chains, CD28, CD3ε, CD45, CD4, CD5, CD8, CD9, CD16, CD22, CD33, CD37, CD64, CD80, CD86, CD134, CD137, CD154, and GITR and can preferably include a polypeptide of a human CD8 transmembrane region. CAR is anchored to the cell membranes of a T cell by this transmembrane region.

The transmembrane region may comprise a hinge region that consists of an arbitrary oligopeptide or polypeptide and has a length of 1 to 100 amino acids, preferably 10 to 70 amino acids. Examples of the hinge region can include a human CD8 hinge region.

A spacer region consisting of an arbitrary oligopeptide or polypeptide may be located between the single chain antibody that recognizes a cell surface antigen on a cancer cell and the transmembrane region or between the transmembrane region and the T cell activation signal transduction region. Examples of the length of the spacer region can include 1 to 100 amino acids, preferably 10 to 50 amino acids. Examples of such a spacer region can include glycine-serine consecutive sequences.

In the present invention, the nucleic acid encoding a T cell function-enhancing factor is not particularly limited as long as the nucleic acid is a nucleic acid encoding IL-7 and a nucleic acid encoding CCL19 (hereinafter, also collectively referred to as "present nucleic acid 1"), a nucleic acid encoding a dominant negative mutant of SHP-1 (hereinafter, also referred to as "present nucleic acid 2"), or a nucleic acid encoding a dominant negative mutant of SHP-2 (hereinafter, also referred to as "present nucleic acid 3"). The nucleic acid may comprise a plurality of nucleic acids selected from the present nucleic acids 1 to 3 and may specifically comprise the present nucleic acid 1 and the present nucleic acid 2, the present nucleic acid 1 and the present nucleic acid 3, the present nucleic acid 2 and the present nucleic acid 3, the present nucleic acid 1 and the present nucleic acid 2 and the present nucleic acid 3.

The nucleic acid encoding IL-7 and the nucleic acid encoding CCL19 in the present nucleic acid 1 can comprise a nucleic acid encoding IL-7 and a nucleic acid encoding CCL19, and the nucleic acid encoding CCL19 may be located upstream or downstream of the nucleic acid encoding IL-7.

The nucleic acid encoding a dominant negative mutant of SHP1 is not particularly limited as long as the nucleic acid encodes a SHP1 mutant that works dominantly over SHP1 and can inhibit the effect of SHP1. Examples thereof can include a nucleic acid encoding a mutant that consists of an amino acid sequence derived from the amino acid sequence of SHP1 by the substitution of at least one amino acid by another amino acid and can inhibit the effect of SHP1. The nucleic acid encoding a dominant negative mutant of SHP2 is not particularly limited as long as the nucleic acid encodes a SHP2 mutant that works dominantly over SHP2 and can inhibit the effect of SHP2. Examples thereof can include a nucleic acid encoding a mutant that consists of an amino acid sequence derived from the amino acid sequence of SHP2 by the substitution of at least one amino acid by another amino acid and can inhibit the effect of SHP2.

The CAR expression vector of the present invention may comprise an arbitrary nucleic acid between the nucleic acid encoding a chimeric antigen receptor and the nucleic acid encoding a T cell immune function-enhancing factor, between a plurality of nucleic acids selected from the present nucleic acid 1, the present nucleic acid 2, and the present nucleic acid 3, or between the nucleic acid encoding IL-7 and the nucleic acid encoding CCL19 in the present nucleic acid 1 as long as each nucleic acid can be expressed. These nucleic acids are preferably linked via a sequence encoding a self-cleaving peptide (2A peptide) or IRES (internal ribozyme entry site), preferably a sequence encoding 2A peptide. The linkage using this sequence enables the efficient expression of each nucleic acid.

The 2A peptide is a virus-derived self-cleaving peptide and is characterized in that G-P (position of 1 residue from the C terminus) in the amino acid sequence represented by SEQ ID NO: 1 is cleaved in the endoplasmic reticulum (Szymczak et al., Expert Opin. Biol. Ther. 5 (5): 627-638 (2005)). Therefore, nucleic acids incorporated to flank the 2A peptide are intracellularly expressed independently from each other.

The 2A peptide is preferably 2A peptide derived from picornavirus, rotavirus, insect virus, Aphthovirus, or *Trypanosoma* virus, more preferably picornavirus-derived 2A peptide (F2A) shown in SEQ ID NO: 2.

The nucleic acid encoding a chimeric antigen receptor can be prepared by a technique known in the art, such as a chemical synthesis method or a PCR amplification method, on the basis of nucleotide sequences encoding the polypeptides of the single chain antibody against a cell surface antigen on a cancer cell, the transmembrane region, and the T cell activation signal transduction region. Selected codons for encoding amino acids may be modified in order to optimize nucleic acid expression in a host cell of interest.

Information on the nucleotide sequences encoding the polypeptides of the single chain antibody against a cell surface antigen on a cancer cell, the transmembrane region, and the T cell activation signal transduction region can be appropriately obtained from documents known in the art or by database search of NCBI (http://www.ncbi.nlm.nih.gov/guide/) or the like.

For example, information on nucleotide sequences encoding polypeptides of CD28, 4-1BB, and CD3ζ transmembrane regions in the T cell activation signal transduction region can be appropriately obtained by database search of NCBI or the like. Examples thereof can include sequences registered under GenBank No: NM_006139.2 (updated date: May 10, 2014) for human CD28, GenBank No: NM_001561.5 (updated date: Mar. 16, 2014) for human 4-1BB, and GenBank No: NM_000734.3 (updated date: Aug. 12, 2014) for human CD3ζ.

Information on a nucleotide sequence encoding a polypeptide of a human CD8 transmembrane region can be appropriately obtained by database search of NCBI or the like. Examples thereof can include a sequence registered under GenBank No: NM_001768.6 (updated date: May 10, 2014).

Information on the nucleotide sequence encoding the polypeptide of the single chain antibody can also be obtained by preparing a monoclonal antibody that recognizes the target cell surface antigen, determining the amino acid sequence of the monoclonal antibody by a method known in the art such as the Edman method, and acquiring the information on the basis of the amino acid sequence. Examples of the method for preparing the monoclonal antibody can include a preparation method using hybridomas, a preparation method which involves transforming a host with an expression vector containing the antibody gene by a genetic engineering approach, and a preparation method which involves immunizing a transgenic animal with the desired antigen.

The nucleic acid encoding a T cell immune function-enhancing factor, i.e., the nucleic acid encoding IL-7 and the nucleic acid encoding CCL19, the nucleic acid encoding a dominant negative mutant of SHP-1, or the nucleic acid encoding a dominant negative mutant of SHP-2, can be prepared by a technique known in the art, such as a chemical synthesis method or a PCR amplification method, on the basis of their respective nucleotide sequences. Selected codons for encoding amino acids may be modified in order to optimize nucleic acid expression in a host cell of interest.

Information on the nucleic acid encoding IL-7 and the nucleic acid encoding CCL19, the nucleic acid encoding a dominant negative mutant of SHP-1, or the nucleic acid encoding a dominant negative mutant of SHP-2 can be appropriately obtained from documents known in the art or by database search of NCBI (http://www.ncbi.nlm.nih.gov/guide/) or the like.

The nucleic acid encoding IL-7 can be appropriately selected according to the type of a cell to which the CAR expression vector of the present invention is transferred. Examples thereof can include a nucleic acid encoding the amino acid sequence (SEQ ID NO: 3) of human IL-7. A nucleotide sequence having 80% or higher, preferably 85% or higher, more preferably 90% or higher, further preferably 95% or higher, most preferably 98% or higher identity to the nucleotide sequence shown in SEQ ID NO: 3 may be used as long as the cell proliferation rate-enhancing effect of IL-7 is maintained.

The nucleic acid encoding CCL19 can be appropriately selected according to the type of a cell to which the CAR expression vector of the present invention is transferred. Examples thereof can include a nucleic acid encoding the amino acid sequence (SEQ ID NO: 4) of human CCL19. A nucleotide sequence having 80% or higher, preferably 85% or higher, more preferably 90% or higher, further preferably 95% or higher, most preferably 98% or higher identity to the nucleotide sequence shown in SEQ ID NO: 4 may be used as long as the chemoattractive effect of CCL19 on a T cell is maintained.

The nucleic acid encoding a dominant negative mutant of SHP-1 can be appropriately selected according to the type of a cell to which the CAR expression vector of the present invention is transferred. Examples thereof can include a nucleic acid encoding the amino acid sequence (SEQ ID NO: 5) of a dominant negative mutant of human SHP-1. A nucleotide sequence having 80% or higher, preferably 85% or higher, more preferably 90% or higher, further preferably 95% or higher, most preferably 98% or higher identity to the nucleotide sequence shown in SEQ ID NO: 5 may be used as long as the dominant negative mutant of SHP-1 can inhibit the effect of SHP-1. In SEQ ID NO: 5, serine at position 453 is a mutated site.

The nucleic acid encoding a dominant negative mutant of SHP-2 can be appropriately selected according to the type of a cell to which the CAR expression vector of the present invention is transferred. Examples thereof can include a nucleic acid encoding the amino acid sequence (SEQ ID NO: 6) of a dominant negative mutant of human SHP-2. A nucleotide sequence having 80% or higher, preferably 85% or higher, more preferably 90% or higher, further preferably 95% or higher, most preferably 98% or higher identity to the nucleotide sequence shown in SEQ ID NO: 6 may be used as long as the dominant negative mutant of SHP-2 can inhibit the effect of SHP-2. In SEQ ID NO: 6, serine at position 459 is a mutated site.

The CAR expression vector of the present invention may be linear or circular and may be a non-viral vector such as a plasmid, a viral vector, or a vector based on a transposon. Such a vector may contain control sequences such as a promoter and a terminator, and a selective marker sequence such as a drug resistance gene or a reporter gene. The nucleic acid encoding CAR or the nucleic acid encoding a T cell immune function-enhancing factor is operably located downstream of the promoter sequence so that each nucleic acid can be efficiently transcribed. Furthermore, the expression of the nucleic acid encoding a chimeric antigen receptor can be easily confirmed owing to the marker gene contained therein.

The CAR expression vector of the present invention may contain a nucleic acid encoding a suicide gene. The position of the suicide gene is not particularly limited, and the suicide gene may be located, via a sequence encoding 2A peptide or IRES, downstream of the promoter for the expression of the nucleic acid encoding IL-7, the nucleic acid encoding CCL19, the nucleic acid encoding a dominant negative mutant of SHP-1, or the nucleic acid encoding a dominant negative mutant of SHP-2 and upstream or downstream of each of these nucleic acids, or may be located downstream of an additional promoter. The CAR expression vector of the present invention containing the nucleic acid encoding a suicide gene enables the control of the number of a CAR-expressing T cell in vivo by administering a drug activating the functions of the suicide gene according to the course of treatment of cancer, for example, when tumor has disappeared.

Examples of the suicide gene can include herpes simplex virus thymidine kinase (HSV-TK) and inducible caspase 9 genes described in documents given below. Examples of the drugs activating the functions of these genes can include ganciclovir for the former and a CID (chemical induction of dimerization) compound AP1903 for the latter (Cooper L J., et al., Cytotherapy. 2006; 8 (2): 105-17; Jensen M. C. et al., Biol Blood Marrow Transplant. 2010 September; 16 (9): 1245-56; Jones B S. Front Pharmacol. 2014 Nov. 27; 5: 254; Minagawa K., Pharmaceuticals (Basel). 2015 May 8; 8 (2): 230-49; and Bole-Richard E., Front Pharmacol. 2015 Aug. 25; 6: 174).

Examples of the viral vector can include retrovirus vectors, lentivirus vectors, adenovirus vectors, and adeno-associated virus vectors and can preferably include retrovirus vectors, more preferably a pMSGV vector (Tamada k et al., Clin Cancer Res 18: 6436-6445 (2002)) and a pMSCV vector (manufactured by Takara Bio Inc.). By use of a retrovirus vector, a transgene is integrated into the genomes of a host cell and can therefore be expressed stably for a long period.

The CAR-expressing T cell of the present invention is not particularly limited as long as the CAR-expressing T cell is a T cell obtained by the transfer of (a) the CAR expression vector of the present invention or a T cell obtained by the transfer of (b) at least two vectors: a CAR expression vector containing a nucleic acid encoding CAR and a nucleic acid encoding interleukin-7 (CAR-IL-7 expression vector) and a CAR expression vector containing a nucleic acid encoding CAR and a nucleic acid encoding CCL19 (CAR-CCL19 expression vector). Examples of the method for transferring the CAR expression vector of the present invention or the CAR-IL-7 expression vector and the CAR-CCL19 expression vector to a T cell can include, but are not particularly limited to, transfer methods by methods known in the art, such as a viral infection method, a calcium phosphate method, lipofection, microinjection, and electroporation and can preferably include a viral infection method. The CAR-IL-7 expression vector can contain the nucleic acid encoding CAR and the nucleic acid encoding interleukin-7. The CAR-CCL19 expression vector can contain the nucleic acid encoding CAR and the nucleic acid encoding CCL19. As with the CAR expression vector of the present invention, these expression vectors may each contain an additional nucleic acid such as a nucleic acid encoding 2A peptide, IRES, or a suicide gene as long as each nucleic acid can be expressed.

Examples of the viral infection method can include a method which involves transfecting a packaging cell such as GP2-293 cell (manufactured by Takara Bio Inc.), Plat-GP cell (manufactured by Cosmo Bio Co., Ltd.), PG13 cell (ATCC CRL-10686), or PA317 cell (ATCC CRL-9078) with the CAR expression vector of the present invention and a packaging plasmid to prepare recombinant viruses and infecting a T cell with the recombinant viruses. The viral infection method may be performed using a commercially available kit such as Retrovirus packaging Kit Eco (manufactured by Takara Bio Inc.).

The transfer of the CAR expression vector of the present invention to the T cell can be confirmed by examining the expression of CAR by flow cytometry, Northern blotting, Southern blotting, PCR such as RT-PCR, ELISA, or Western blotting, or examining the expression of a marker gene inserted in the vector.

Examples of the T cell can include a human-derived T cell and a non-human mammal (e.g., dog, cat, pig, or mouse)-derived T cell. Alternatively, the T cell can be obtained by isolation and purification from a body fluid such as blood or bone marrow fluid, tissues of the spleen, the thymus, lymph nodes, or the like, or immunocytes infiltrating cancer tissues of primary tumor, metastatic tumor, cancerous ascites, or the like. Examples of such T cell can include αβT cell, γδT cell, CD8+ T cell, CD4+ T cell, tumor-infiltrating T cell, memory T cell, naive T cell, and NKT cell.

The single chain antibody expressed by the CAR-expressing T cell of the present invention is extracellularly positioned. The CAR-expressing T cell having this single chain antibody is capable of recognizing a tumor-associated antigen (TAA) expressed on the surface of cancer cell.

The CAR-expressing T cell of the present invention may harbor a vector containing a nucleic acid encoding a suicide gene in addition to the CAR expression vector of the present invention.

The anticancer agent of the present invention is not particularly limited as long as the anticancer agent comprises the CAR-expressing T cell of the present invention and a pharmaceutically acceptable additive. Examples of the additive can include saline, buffered saline, cell culture media, dextrose, injectable water, glycerol, ethanol, and combinations thereof, stabilizers, solubilizers and surfactants, buffers and antiseptics, tonicity agents, fillers, and lubricants.

The anticancer agent of the present invention can be administered to a test subject in need of treatment of cancer using a method known to those skilled in the art. Examples of the administration method can include intravenous, intratumoral, intracutaneous, subcutaneous, intramuscular, intraperitoneal, intraarterial, intramedullary, intracardiac, intraarticular, intrasynovial, intracranial, intrathecal, and subarachnoidal (spinal fluid) injection.

The amount of the CAR-expressing T cell of the present invention contained in the anticancer agent to be administered can be appropriately adjusted according to the type, position, and severity of cancer, the age, body weight, and condition of the test subject to receive treatment, etc. Examples thereof can preferably include $1 \times 10^4$ to $1 \times 10^{10}$ cells, preferably $1 \times 10^5$ to $1 \times 10^9$ cells, more preferably $5 \times 10^6$ to $5 \times 10^8$ cells, in a single dose.

The anticancer agent to be administered can be independently administered 4 times, 3 times, twice, or once a day, at a 1-day, 2-day, 3-day, 4-day, or 5-day interval, once a week, at a 7-day, 8-day, or 9-day interval, twice a week, once a month, or twice a month.

Examples of the cancer for the anticancer agent of the present invention or a method for treating cancer mentioned later can include: cancers such as adenocarcinoma, squamous cell cancer, adenosquamous cancer, undifferentiated cancer, large-cell cancer, small-cell cancer, skin cancer, breast cancer, prostate cancer, urinary bladder cancer, vaginal cancer, neck cancer, uterine cancer, liver cancer, kidney cancer, pancreatic cancer, spleen cancer, lung cancer, tracheal cancer, bronchial cancer, colon cancer, small intestine cancer, stomach cancer, esophageal cancer, gallbladder cancer, testis cancer, and ovary cancer; cancers of bone tissues, cartilage tissues, fat tissues, muscle tissues, vascular tissues, and hematopoietic tissues; sarcomas such as chondrosarcoma, Ewing's sarcoma, malignant hemangioendothelioma, malignant schwannoma, osteosarcoma, and soft tissue sarcoma; blastomas such as hepatoblastoma, medulloblastoma, nephroblastoma, neuroblastoma, pancreatoblastoma, pleuropulmonary blastoma, and retinoblastoma; embryonic cell tumor; lymphoma; and leukemia.

The anticancer agent of the present invention can be used in combination with an additional anticancer agent. Examples of the additional anticancer agent can include: alkylating agents such as cyclophosphamide, bendamustine, Ifosfamide, and dacarbazine; antimetabolites such as pentostatin, fludarabine, cladribine, methotrexate, 5-fluorouracil, 6-mercaptopurine, and enocitabine; molecular targeting drugs such as rituximab, cetuximab, and trastuzumab; kinase inhibitors such as imatinib, gefitinib, erlotinib, afatinib, dasatinib, sunitinib, and trametinib; proteasome inhibitors such as bortezomib; calcineurin inhibitors such as cyclosporine and tacrolimus; anticancer antibiotics such as idarubicin, doxorubicin mitomycin C; vegetable alkaloids such as irinotecan and etoposide; platinum-containing drugs such as cisplatin, oxaliplatin, and carboplatin; hormone therapeutics such as tamoxifen and bicalutamide; and immunoregulatory drugs such as interferon, nivolumab, and pembrolizumab and can preferably include alkylating agents and antimetabolites, more preferably cyclophosphamide.

The method for "using the anticancer agent of the present invention in combination with the additional anticancer agent" can include a method using the additional anticancer agent in the treatment, followed by use of the anticancer agent of the present invention, a method concurrently using the anticancer agent of the present invention and the additional anticancer agent, and a method using the anticancer agent of the present invention in the treatment, followed by use of the additional anticancer agent and can preferably include a method using the additional anticancer agent in the treatment, followed by use of the anticancer agent of the present invention. The combined use of the anticancer agent of the present invention and the additional anticancer agent further improves therapeutic effects on cancer and can also reduce the adverse effects of each anticancer agent by decreasing the administration frequency or dose of the anticancer agent. Also, the additional anticancer agent may be contained in the anticancer agent of the present invention.

Examples of alternative aspect 1 of the present invention can include 1) a method for treating cancer, comprising administering the CAR-expressing T cell of the present invention to a patient in need of treatment of cancer, 2) the CAR-expressing T cell of the present invention for use as an anticancer agent, and 3) use of the CAR-expressing T cell of the present invention for the preparation of an anticancer agent.

Examples of alternative aspect 2 of the present invention can include a kit for the preparation of CAR-expressing T cell, comprising the CAR expression vector of the present invention. The kit is not particularly limited as long as the kit comprises the CAR expression vector of the present invention. The kit may comprise an instruction manual for the preparation of CAR-expressing T cells, and a reagent for use in the transfer of the CAR expression vector of the present invention to T cells.

Example 1

[Preparation of T Cells Expressing IL-7 and CCL19]
(Selection of T Cell Immune Function-Enhancing Factor)

At least several hundred different types of molecules that can control the functions of T cells are present in vivo. The inventors first selected IL-7 and CCL19 from among an enormous number of combinations on the basis of the previous findings or experiments, as control molecules for further enhancing the antitumor effect of CAR-T cells, and also selected the combination of these two molecules, i.e., the combination of IL-7 and CCL19, not each alone. The inventors prepared a vector for the coexpression of these T cell immune function-enhancing factors and CAR.

The IL-7 is a cytokine essential for the survival of T cells and is produced by non-hematopoietic cells such as stromal cells of the bone marrow, the thymus, and lymphatic organs or tissues. On the other hand, T cells themselves are hardly found to have the ability to produce IL-7.

The CCL19 is mainly produced from dendritic cells or macrophages of lymph nodes and has the function of evoking the migration of T cells, B cells, or matured dendritic cells via its receptor CCR7.

(Preparation of Anti-FITC CAR Expression Vector for Expression of IL-7 and CCL19)

An anti-FITC CAR DNA fragment (SEQ ID NO: 7) encoding anti-FITC CAR consisting of anti-FITC scFv, a mouse CD8 transmembrane region, and mouse CD28-4-1BB-CD3ζ intracellular signal motifs, a F2A-MCS DNA fragment (SEQ ID NO: 8) encoding 2A peptide (F2A) shown in SEQ ID NO: 1 and a multicloning site (MCS) following the peptide, and an IL-7-F2A-CCL19 DNA fragment (SEQ ID NO: 9) encoding mouse IL-7 (without a stop codon) and F2A and mouse CCL19 following the mouse IL-7 were artificially synthesized. In SEQ ID NO: 7, positions 1 to 819 represent a sequence encoding the polypeptide of the anti-FITC scFv, positions 829 to 1074 represent a sequence encoding the polypeptide of the mouse CD8 transmembrane region, positions 1075 to 1197 represent a sequence encoding the polypeptide of the mouse CD28 intracellular region, positions 1198 to 1332 represent a sequence encoding the polypeptide of the 4-1BB intracellular region, and positions 1333 to 1674 represent a sequence encoding the polypeptide of the CD3ζ intracellular region. In SEQ ID NO: 9, positions 1 to 462 represent a sequence encoding the IL-7, positions 463 to 537 represent a sequence encoding the F2A, and positions 538 to 864 represent a sequence encoding the CCL19.

In order to prepare a CAR vector for the expression of CAR, IL-7, and CCL19, the anti-FITC CAR DNA fragment and the F2A-MCS DNA fragment were linked to prepare an anti-FITC CAR-F2A-MCS construct. Then, the prepared construct was cloned into a pMSGV retrovirus expression vector (Tamada k et al., Clin Cancer Res 18: 6436-6445 (2002)) to prepare a pMSGV vector containing anti-FITC CAR-F2A-MCS. The IL-7-F2A-CCL19 DNA fragment was inserted to the MCS of the pMSGV vector by restriction enzyme (NsiI and SalI) treatment and ligation to obtain a pMSGV vector containing anti-FITC CAR-F2A-IL-7-F2A-CCL19 (IL-7/CCL19 expression-anti-FITC CAR vector). The map of the obtained vector is shown in FIG. 2. Also, the anti-FITC CAR DNA fragment was cloned into a pMSGV retrovirus expression vector to prepare a pMSGV vector containing anti-FITC CAR as a control (control anti-FITC CAR vector).

(Preparation of Retrovirus Harboring IL-7/CCL19 Expression-Anti-FITC CAR Vector)

For the transduction of mouse T cells, retrovirus was prepared. A GP2-293 packaging cell line (manufactured by Takara Bio Inc.) was transfected with the aforementioned IL-7/CCL19 expression-anti-FITC CAR vector or control anti-FITC CAR vector and a pCL-Eco plasmid (manufactured by Imgenex Corp.) using Lipofectamine 2000 or 3000 (manufactured by Life Technologies Corp.) to prepare retrovirus harboring the IL-7/CCL19 expression-anti-FITC CAR vector or the control anti-FITC CAR vector. After 48 hours from the transfection, a supernatant containing the retrovirus was recovered.

DMEM supplemented with 10% FCS, 100 U/ml penicillin, and 100 mg/ml streptomycin was used as a culture medium for the GP2-293 cells. RPMI-1640 supplemented with 10% FCS, 100 U/ml penicillin, 100 mg/ml streptomycin, 50 mM 2-mercaptoethanol, and 2 mM L-glutamine was used as a culture medium for T cells used in Examples mentioned later.

(Transduction of Mouse T Cells)

For the transduction of mouse T cells, $3\times10^6$ purified mouse T cells derived from the spleen and lymph nodes were activated for 48 hours with an immobilized anti-CD3 monoclonal antibody (3 μg/ml), anti-CD28 monoclonal antibody (1 μg/ml), and IL-2 (100 IU/ml). Then, the supernatant containing the thus-prepared retrovirus harboring the IL-7/CCL19 expression-anti-FITC CAR vector or the control anti-FITC CAR vector was mixed with the activated mouse T cells ($1\times10^6$ cells/ml) in a plate coated with 25 μg/ml RetroNectin® (manufactured by Takara Bio Inc.). After centrifugation at 1500 rpm for 2 hours, the cells were cultured for 6 hours in the presence of IL-2 (100 IU/ml). In order to remove the retrovirus from the culture medium, the mouse T cells were recovered, transferred to a fresh growth culture medium (RPMI) containing IL-2 (100 IU/ml), and further cultured for 42 hours to obtain mouse T cells harboring the IL-7/CCL19 expression-anti-FITC CAR vector (anti-FITC CAR-IL-7/CCL19-expressing T cells) or mouse T cells harboring the control anti-FITC CAR vector (anti-FITC CAR-expressing T cells).

(Preparation of Anti-CD20 CAR Expression Vector for Expression of IL-7 and CCL19)

A pMSGV vector containing anti-human CD20 CAR-F2A-IL-7-F2A-CCL19 (IL-7/CCL19 expression-anti-human CD20 CAR vector) was prepared in the same way as in the preparation of the IL-7/CCL19 expression-anti-FITC CAR vector described above except that the sequence of the anti-FITC scFv region contained in the sequence represented by SEQ ID NO: 7 was replaced with a sequence of anti-human CD20 scFv (SEQ ID NO: 10) synthesized by Life Technologies Corp. on the basis of the sequence of rituximab. Likewise, a pMSGV vector containing anti-human CD20 CAR (control anti-human CD20 CAR vector) was prepared in the same way as in the preparation of the control anti-FITC CAR vector described above except that the sequence of the anti-FITC scFv region contained in the sequence represented by SEQ ID NO: 7 was replaced with the sequence of anti-human CD20 scFv (SEQ ID NO: 10). The IL-7/CCL19 expression-anti-human CD20 CAR vector or the control anti-human CD20 CAR vector was transferred to mouse T cells in the same way as above to prepare anti-human CD20 CAR-IL-7/CCL19-expressing T cells or anti-human CD20 CAR-expressing T cells.

Example 2

[CAR Expression Assay by Flow Cytometry]
(Flow Cytometry Analysis)

The expression level of CAR recognizing FITC as a model antigen was analyzed by two-color flow cytometry. The prepared anti-FITC CAR-IL-7/CCL19-expressing T cells were cultured in the presence of FITC-bound dextran and an allophycocyanin (APC)-bound anti-CD8 monoclonal antibody (53-6.7 manufactured by Affymetrix, Inc.). EC800 (manufactured by Sony Corp.) was used in the flow cytometry, and the data was analyzed using FlowJo software (manufactured by Tree Star, Inc.).

The expression level of CAR recognizing human CD20 was also analyzed by two-color flow cytometry. The prepared anti-human CD20 CAR-IL-7/CCL19-expressing T cells were analyzed using biotinylated protein L and APC-bound streptavidin.
(Results)

The results are shown in FIGS. 3 to 5. In FIG. 3, the left graph depicts the results about an unstained CAR sample (FITC-bound dextran was not added) of the anti-FITC CAR-IL-7/CCL19-expressing T cells, and the right graph depicts the results about a stained CAR sample (FITC-bound dextran was added) of the anti-FITC CAR-IL-7/CCL19-expressing T cells. In FIG. 4, "transduction (−)" depicts the results about untransduced T cells, "Cont." depicts the results about the anti-FITC CAR-expressing T cells, and "7×19" depicts the results about the anti-FITC CAR-IL-7/CCL19-expressing T cells. In FIG. 5, "transduction (−)" depicts the results about untransduced T cells, "Cont." depicts the results about the anti-human CD20 CAR-expressing T cells, and "7×19" depicts the results about the anti-human CD20 CAR-IL-7/CCL19-expressing T cells. The numerical values in these drawings represent the percentage of each population. As shown in FIGS. 3 to 5, the expression of CAR was confirmed in the anti-FITC CAR-IL-7/CCL19-expressing T cells and the anti-human CD20 CAR-IL-7/CCL19-expressing T cells.

Example 3

[Secretion of IL-7 and CCL19]
(Measurement of IL-7 and CCL19 Concentrations in Culture Supernatant of Anti-FITC CAR-IL-7/CCL19-Expressing T Cells-1)

The prepared anti-FITC CAR-IL-7/CCL19-expressing T cells or anti-FITC CAR-expressing T cells were stimulated with 1 μg/ml immobilized FITC-bound trastuzumab and cultured for 3 days. The supernatant was recovered, and the concentrations of IL-7 and CCL19 were measured using a commercially available ELISA kit (manufactured by R&D systems, Inc.). The results are shown in FIG. 6.
(Results)

As shown in FIG. 6, in the culture supernatant, IL-7 was detected at 300 pg/ml or larger, and CCL19 was detected at 75 pg/ml or larger. Thus, it was confirmed that: the anti-FITC CAR-IL-7/CCL19-expressing T cells express IL-7 and CCL19; and the expressed IL-7 and CCL19 are secreted to the outside of the cells. IL-7 and CCL19 from the control anti-FITC CAR-expressing T cells both fell below the detection limit (Not detected).
(Measurement of IL-7 and CCL19 Concentrations in Culture Supernatant of Anti-FITC CAR-IL-7/CCL19-Expressing T Cells-2)

The concentrations of IL-7 and CCL-19 after culture for 3, 5, or 7 days with or without stimulation with immobilized FITC-bound trastuzumab or an anti-CD3 monoclonal antibody were measured using the ELISA kit. The results are shown in FIG. 7. In FIG. 7, the open column shows the results obtained without stimulation, the gray column shows the results obtained with stimulation with FITC-bound trastuzumab, and the filled column shows the results obtained with stimulation with an anti-CD3 monoclonal antibody. "Cont." depicts the results about the anti-FITC CAR-expressing T cells, and "7×19" depicts the results about the anti-FITC CAR-IL-7/CCL19-expressing T cells.
(Results)

As is evident from FIG. 7, the anti-FITC CAR-IL-7/CCL19-expressing T cells were shown to secrete IL-7 and CCL-19 to the outside of the cells by culture not only for 3 days but for 5 days or 7 days.
(Measurement of IL-7 and CCL19 Concentrations in Culture Supernatant of Anti-Human CD20 CAR-IL-7/CCL19-Expressing T Cells)

As for the prepared anti-human CD20 CAR-IL-7/CCL19-expressing T cells or anti-human CD20 CAR-expressing T cells, the concentrations of IL-7 and CCL-19 after culture for 3 days or 5 days with or without simulation with P815 mastocytoma treated with mitomycin C, P815 mastocytoma genetically recombined to express human CD20 (P815-hCD20), or an immobilized anti-CD3 monoclonal antibody were similarly measured using the ELISA kit. The results are shown in FIG. 8. In FIG. 8, the open column shows the results obtained without stimulation, the diagonally shaded column shows the results obtained with stimulation with P815 treated with mitomycin C, the filled column shows the results obtained with stimulation with P815-hCD20, and the gray column shows the results obtained with stimulation with an immobilized anti-CD3 monoclonal antibody. "Cont." depicts the results about the anti-human CD20 CAR-expressing T cells, and "7×19" depicts the results about the anti-human CD20 CAR-IL-7/CCL19-expressing T cells.
(Results)

As is evident from FIG. 8, the anti-human CD20 CAR-IL-7/CCL19-expressing T cells were also shown to secrete IL-7 and CCL-19 to the outside of the cells.

Example 4

[Cell Number and Survival Rate of CAR-Expressing T Cells]
(Cell Number and Survival Rate of Anti-FITC CAR-IL-7/CCL19-Expressing T Cells)

Study was conducted on whether IL-7 or CCL19 produced by the anti-FITC CAR-IL-7/CCL19-expressing T cells would exert biological functions and exhibit an immunity-inducing effect. The prepared anti-FITC CAR-IL-7/CCL19-expressing T cells or anti-FITC CAR-expressing T cells were stimulated with 1 μg/ml immobilized FITC-bound trastuzumab and cultured for 3 days, 5 days, or 7 days, and the cells and the supernatant were recovered. The cell number and the survival rate were analyzed by trypan blue staining. The results are shown in FIGS. 9 and 10. In FIGS. 9 and 10, the filled column shows the results about the anti-FITC CAR-IL-7/CCL19-expressing T cells, the open column shows the results about the anti-FITC CAR-expressing T cells, and the abscissa shows the number of culture days. Statistically significant difference was studied by the Student's t-test (* $p<0.05$,  $p<0.01$, * $p<0.005$, †$p<0.001$).
(Results)

As shown in FIGS. 9 and 10, the cell proliferation and the survival rate of the anti-FITC CAR-IL-7/CCL19-expressing T cells were both enhanced, demonstrating that IL-7 and CCL19 produced by the anti-FITC CAR-IL-7/CCL19-expressing T cells exert biological functions.
(Cell Number of Anti-Human CD20 CAR-IL-7/CCL19-Expressing T Cells)

A sample containing the anti-human CD20 CAR-IL-7/CCL19-expressing T cells ($4\times10^5$ cells) was costimulated with mitomycin C and P815-hCD20 in the presence of a rat IgG2a isotype control, an anti-CD127 monoclonal neutralizing antibody, or an anti-CCR7 monoclonal neutralizing antibody. The cells were cultured for 5 days, and the absolute number of live cells was examined using trypan blue. CD127 is an IL-7 receptor, and CCR7 is a CCL19 receptor. The results are shown in FIG. 11. In FIG. 11, "Iso.Cntrl." depicts the results obtained by the stimulation with P815-hCD20 in the presence of the rat IgG2a isotype control, "anti-CD127" depicts the results obtained by the stimulation with P815-hCD20 in the presence of the anti-CD127 monoclonal neutralizing antibody, and "anti-CCR7" depicts the results obtained by the stimulation with P815-hCD20 in the presence of the anti-CCR7 monoclonal neutralizing antibody. In FIG. 11, the filled column shows the results about the anti-human CD20 CAR-IL-7/CCL19-expressing T cells, and the open column shows the results about the anti-human CD20 CAR-expressing T cells. Each data was indicated by mean±standard deviation from 3 wells. *: $P<0.05$, †: $P<0.001$.

(Results)

As shown in FIG. 11, the cell number of the anti-human CD20 CAR-IL-7/CCL19-expressing T cells was also increased, and their cell proliferation rate was enhanced while the cell proliferation was inhibited by anti-CD127, demonstrating that the enhancement in cell proliferation rate works via the IL-7 receptor CD127.

Example 5

[T Cell Migration Test]
(T Cell Migration Test Using Anti-FITC CAR-IL-7/CCL19-Expressing T Cells)

The chemoattractive effect of CCL19 was studied by a cell migration test using Transwell. The migration properties of responder T cells were measured by migration through a polycarbonate filter having a pore size of 5 μm using 96-well Transwell® chambers (Costar, manufactured by Corning, Inc.). Specifically, the anti-FITC CAR-IL-7/CCL19-expressing T cells or the anti-FITC CAR-expressing T cells were stimulated for 3 days with 1 μg/ml immobilized FITC-bound trastuzumab in the lower chamber. The responder T cells were prepared from the spleen or lymph nodes by negative selection using MACS® (manufactured by Miltenyi Biotec GmbH). The responder T cells were labeled with CytoTell blue (manufactured by AAT Bioquest, Inc.) and cultured for 3 hours in the upper layer. The migration from the upper chamber to the lower chamber was examined by flow cytometry. The results are shown in FIG. 12. In FIG. 12, the filled column shows the results about the anti-FITC CAR-IL-7/CCL19-expressing T cells, the open column shows the results about the anti-FITC CAR-expressing T cells, and the ordinate shows the absolute number of responder T cells that migrated to the lower chamber (the same holds true for FIGS. 13 and 14 below). Statistically significant difference was studied by the Student's t-test (* $p<0.05$).

(Results)

As shown in FIG. 12, the anti-FITC CAR-IL-7/CCL19-expressing T cells allowed a larger number of T cells to migrate to the lower chamber as compared with the anti-FITC CAR-expressing T cells. In lymphocyte (e.g., CAR-expressing T cell) transfer therapy, damage to cancer cells by administered T cells is important as a matter of course, and in addition, it is important to activate endogenous T cells (=host's immunocytes) originally present in a cancer patient and thereby recruit these cells as cells attacking the cancer cells. For this purpose, it is preferred not only to transfer lymphocytes having antitumor activity ab extra but to evoke the active interaction between the transferred T cells and the endogenous T cells by some approach so that the endogenous T cells are accumulated locally to cancer, from the viewpoint of enhancing immunotherapeutic effects. As seen from the results of FIG. 12, the anti-FITC CAR-IL-7/CCL19-expressing T cells had the ability to accumulate intrinsic T cells, demonstrating that the active interaction between the transferred T cells and the endogenous T cells can be induced.

(Migration Test of T Cells or Dendritic Cells Using Anti-FITC CAR-IL-7/CCL19-Expressing T Cells)

A sample containing the anti-FITC CAR-IL-7/CCL19-expressing T cells or the anti-FITC CAR-expressing T cells ($5\times10^5$ cells) was stimulated with immobilized FITC-bound trastuzumab or an anti-CD3 monoclonal antibody in the lower chamber of Transwell. On day 3, $4\times10^5$ T cells stained with CytoTell Blue were placed on the upper chamber and incubated for 3 hours or 5 hours. Likewise, each sample was stimulated with immobilized FITC-bound trastuzumab. On day 3, $4\times10^5$ dendritic cells stained with CytoTell Blue were placed on the upper chamber and incubated for 3 hours. The responder cells of each type that migrated from the upper chamber to the lower chamber were analyzed by flow cytometry. The results are shown in FIGS. 13 and 14. In FIGS. 13 and 14, the filled column shows the results about the anti-FITC CAR-IL-7/CCL19-expressing T cells, and the open column shows the results about the anti-FITC CAR-expressing T cells. In FIGS. 13 and 14 and FIG. 15 mentioned later, each data was indicated by mean±standard deviation from 3 wells. *: $P<0.05$, **: $P<0.01$, †: $P<0.001$, ††: $P<0.00001$, ‡: $P<5\times10^{-5}$.

(Results)

The results of FIGS. 13 and 14 demonstrated that the anti-FITC CAR-IL-7/CCL19-expressing T cells have the high ability to accumulate intrinsic T cells and dendritic cells.

(T Cell Migration Test Using Anti-Human CD20 CAR-IL-7/CCL19-Expressing T Cells)

A sample containing the anti-human CD20 CAR-IL-7/CCL19-expressing T cells ($1\times10^5$ cells) was cocultured with P815-hCD20 treated with mitomycin C in the lower chamber of Transwell. On day 3, $4\times10^5$ T cells stained with CytoTell Blue were placed on the upper chamber and incubated for 3 hours in the presence of a rat IgG2a isotype control, an anti-CD127 monoclonal antibody, or an anti-CCR7 monoclonal antibody. The responder T cells that migrated from the upper chamber to the lower chamber were analyzed by flow cytometry. The results are shown in FIG. 15. In FIG. 15, "Iso.Cntrl." depicts the results obtained by the stimulation with P815-hCD20 in the presence of the rat IgG2a isotype control, "anti-CD127" depicts the results obtained by the stimulation with P815-hCD20 in the presence of the anti-CD127 monoclonal neutralizing antibody, and "anti-CCR7" depicts the results obtained by the stimulation with P815-hCD20 in the presence of the anti-CCR7 monoclonal neutralizing antibody. In FIG. 15, the filled column shows the results about the anti-human CD20 CAR-IL-7/CCL19-expressing T cells, and the open column shows the results about the anti-human CD20 CAR-expressing T cells.

(Results)

As seen from the results of FIG. 15, the anti-human CD20 CAR-IL-7/CCL19-expressing T cells also had the high ability to accumulate intrinsic T cells, and the accumulation of the intrinsic T cells was inhibited by anti-CCR7, demonstrating that the accumulation of the intrinsic T cells works via the CCL19 receptor CCR7.

The results of FIGS. 9 to 15 demonstrated that the anti-FITC CAR-IL-7/CCL19-expressing T cells and the anti-human CD20 CAR-IL-7/CCL19-expressing T cells possess important effects, indispensable for the induction of immunity, of effectively proliferating by IL-7, having a high survival rate, and locally accumulating T cells or dendritic cells to cancer via CCL19, and have an excellent immunity-inducing effect. In short, the expression of the two control molecules, i.e., "IL-7" and "CCL19", in the CAR-expressing T cells was shown to enable improvement in the proliferative potential, the survival rate, and the immunity-inducing effect of the T cells.

Example 6

[Proliferative Potential of T Cells]

A sample containing the anti-FITC CAR-IL-7/CCL19-expressing T cells or the control anti-FITC CAR-expressing T cells ($5 \times 10^5$ cells) was stained with CytoTell Blue (manufactured by AAT Bioquest, Inc.), stimulated with immobilized FITC-bound trastuzumab, and then analyzed by flow cytometry. The results on day 5 after the start of the stimulation are shown in FIG. 16, and the results on days 3 and 7 after the start of the stimulation are shown in FIG. 17. In FIG. 16, the numerical values on the histograms represent the number of cell division. In FIGS. 16 and 17, the numerical values on the circle graphs represent the ratio of each gated fraction (0, 1, 2, 3, or 4>the number of cell division) to a leukocyte population.

(Results)

The results of FIGS. 16 and 17 demonstrated that the proliferative potential of the anti-FITC CAR-IL-7/CCL19-expressing T cells is increased as compared with the anti-FITC CAR-expressing T cells.

Example 7

[Expression of CD127 or CCR7 in T Cells, Dendritic Cells, and CAR-Expressing T Cells]

Unstimulated spleen T cells (naive T cells), spleen T cells stimulated by culture for 2 days with an anti-CD3 monoclonal antibody, an anti-CD28 monoclonal antibody, and IL-2 (activated T cells), unstimulated spleen dendritic cells (dendritic cells), and anti-FITC CAR-expressing T cells (Cont.) and anti-FITC CAR-IL-7/CCL19-expressing T cells (7×19) prepared by activation in the same way as in "Transduction of mouse T cells" of Example 1 were analyzed by flow cytometry and examined for the expression of CD127 or CDR7. The T cells were a $CD3^+CD19^-$ population, the anti-FITC CAR-expressing T cells and the anti-FITC CAR-IL-7/CCL19-expressing T cells were populations positive to FITC-bound dextran beads, and the dendritic cells were a $CD11c^+$ population. The results of examining the CD127 expression are shown in FIG. 18, and the results of examining the CCR7 expression are shown in FIG. 19. In these drawings, the numerical values represent % of positive cells, "Cont." depicts the results about the anti-FITC CAR-expressing T cells, and "7×19" depicts the results about the anti-FITC CAR-IL-7/CCL19-expressing T cells.

(Results)

As shown in FIG. 18, the expression of CD127 was evidently reduced in the activated T cells as compared with the naive T cells, but was shown to be larger in the anti-FITC CAR-IL-7/CCL19-expressing T cells than in the activated T cells and to be restored cover the naive T cells. As shown in FIG. 19, the expression of CCR7 was reduced by activation in the anti-FITC CAR-IL-7/CCL19-expressing T cells, but was shown to be kept as high as approximately 67% of the expression in the naive T cells. It has heretofore been known that the expression of CD127 or CCR7 is reduced to approximately ½ to ⅓ by the activation of T cells. Therefore, even if CAR-expressing T cells that express IL-7 or CCL19 are prepared, it is considered that the effects of IL-7 and CCL19 are reduced by the activation of the CAR-expressing T cells. Thus, usually, it may not be expected that the expression of IL-7 and CCL19 in CAR-expressing T cells enhances the immunity-inducing effect or the antitumor activity of the CAR-expressing T cells. In this test as well, it was able to be confirmed that the expression of CD127 or CCR7 was temporarily reduced on day 2 post-activation of the spleen T cells. Nonetheless, the expression of CD127 or CCR7 was shown to be restored on day 4 in the anti-FITC CAR-IL-7/CCL19-expressing T cells. This indicates that the expression of IL-7 and CCL19 in the CAR-expressing T cells is useful for potentiating their immunity-inducing effect or antitumor activity.

Example 8

[Therapeutic Effect in Mouse Tumor Models]
(Administration of Anti-Human CD20 CAR-IL-7/CCL19-Expressing T Cells to Mice)

$5 \times 10^5$ P815 mastocytoma cells genetically recombined to express human CD20 (P815-hCD20) were subcutaneously inoculated to each cancer-bearing mouse (DBA/2 mouse). After 3 days, $3 \times 10^6$ anti-human CD20 CAR-IL-7/CCL19-expressing T cells or anti-human CD20 CAR-expressing T cells were intravenously administered to the mouse. A no-treatment group was established as a control by inoculating the P815 mastocytoma to each mouse and not conducting the subsequent treatment (without administration of the CAR-expressing T cells). The mouse tumor volume and survival rate were measured twice a week. In the tumor volume analysis, standard deviation was calculated for each experimental group. Statistically significant difference among the 3 groups was studied by the Student's t-test for the tumor volume analysis and the log-rank test for the survival rate examination (* P<0.05, ** P<0.01).

The results of examining change in the tumor volumes of the mice are shown in FIG. 20, and the results of examining the survival rate of the mice are shown in FIG. 21. In FIGS. 20 and 21, the open circle depicts the results obtained by the administration of the anti-human CD20 CAR-expressing T cells, the filled circle depicts the results obtained by the administration of the anti-human CD20 CAR-IL-7/CCL19-expressing T cells, and the open rhomboid depicts the results obtained without administration of the CAR-expressing T cells in the no-treatment group. In FIG. 20, the abscissa shows days post-intravenous administration of the cells to the mice, and the ordinate shows the tumor volume ($mm^3$). In FIG. 21, the abscissa shows weeks post-intravenous administration of the cells to the mice, and the ordinate shows the survival rate (%).

(Results)

As shown in FIGS. 20 and 21, the administration of the anti-human CD20 CAR-IL-7/CCL19-expressing T cells was confirmed to exhibit the effect of decreasing a tumor volume and improvement in survival rate (effect of prolonging a survival period) as compared with the administration of the anti-human CD20 CAR-expressing T cells or no administration of the CAR-expressing T cells. Thus, the anti-human CD20 CAR-IL-7/CCL19-expressing T cells were shown to have excellent antitumor activity.

(Inoculation of Anticancer Agent and Anti-Human CD20 CAR-IL-7/CCL19-Expressing T Cells to Mice)

5×10⁵ P815-hCD20 cells were subcutaneously inoculated to each mouse. On day 10 post-inoculation, an anticancer agent cyclophosphamide (CPA, 100 mg/kg) was intraperitoneally administered thereto, and on day 14, 1×10⁶ anti-human CD20 CAR-IL-7/CCL19-expressing T cells or anti-human CD20 CAR-expressing T cells were intravenously administered thereto. The results of examining the survival rate of the mice are shown in FIG. 22, and the results of examining their tumor volumes are shown in FIGS. 23 and 24. In FIGS. 22 to 24, the abscissa shows days post-subcutaneous inoculation of P815-hCD20 (the date of subcutaneous inoculation of P815-hCD20 to the mice was defined as day 0), and the ordinate shows the survival rate (FIG. 22) or the tumor volume (Major axis of tumor×(Minor axis of tumor)²/2 (mm³)) (FIGS. 23 and 24). "no treatment" depicts the results obtained in an untreated group, "CPA" depicts the results obtained in a group given CPA alone, "CPA+Cont." depicts the results obtained in the group given the anti-human CD20 CAR-expressing T cells after the CPA administration, "CPA+7×19" depicts the results obtained in the group given the anti-human CD20 CAR-IL-7/CCL19-expressing T cells after the CPA administration, and † depicts the death of a mouse. FIG. 24 is a diagram showing ¹/₁₀ of numerical values on the ordinate of the graph of CPA+7×19 in FIG. 23.

(Results)

As shown in FIG. 22, the combined use of the anti-human CD20 CAR-IL-7/CCL19-expressing T cells of the present invention and the anticancer agent was shown to attain a very high survival rate. As shown in FIGS. 23 and 24, the combined use of the anti-human CD20 CAR-IL-7/CCL19-expressing T cells of the present invention and the anticancer agent was shown to attain complete disappearance of tumor. As shown in FIG. 24, the tumor volume was largest on day 10 post-subcutaneous inoculation of P815-hCD20. In this respect, the minor axis was 4.86 mm to 7.25 mm, the major axis was 5.92 mm to 8.39 mm, and the tumor volume was 69.91 mm³ to 220.50 mm³ with 140.02 mm³ on average. The results described above also indicated that the tumor that proliferated temporarily disappeared by the treatment with the anti-human CD20 CAR-IL-7/CCL19-expressing T cells. In the case of using the CAR-expressing T cells of the present invention in combination with an additional anticancer agent, it is preferred, for further enhancing the antitumor activity of the CAR-expressing T cells of the present invention, to first decrease a lymphocyte cell number by use of the additional anticancer agent and then administer the anti-human CD20 CAR-IL-7/CCL19-expressing T cells, as in the method described above. Such a method can potentiate the in vivo homeostasis of the CAR-expressing T cells.

Example 9

[Effect of Infiltrating into Tumor Tissues]

5×10⁵ P815-hCD20 cells were subcutaneously inoculated to each mouse. On day 3 post-inoculation, 1×10⁶ anti-human CD20 CAR-IL-7/CCL19-expressing T cells were administered thereto. On day 21 post-inoculation, tumor tissues were cut. The tissue of each mouse was divided into two portions. One of these two portions was stained with hematoxylin-eosin (H&E), and the other portion was used in immunohistochemical analysis. The immunohistochemical analysis was conducted using the combination of anti-CD4 and anti-CD8 monoclonal antibodies or the combination of anti-CD3 and anti-DEC205 monoclonal antibodies as primary antibodies. Alexa Fluor® 488-bound anti-rat IgG2a (green) and Alexa Fluor® 647-bound anti-rat IgG2b (red) were used as secondary antibodies. The nuclei of the cells were stained with DAPI (blue). The H&E-stained samples and the immunolabeled fragments were microscopically observed at a magnification of ×100 or ×200. CD4 and CD8 are markers for T cells, and DEC205 is a marker for dendritic cells. The results of the H&E staining are shown in FIG. 25, and the results of the immunohistochemical analysis are shown in FIGS. 26(a) and 26(b). The results of quantifying the positive region labeled by each fluorescent staining (CD4 staining (red), CD8 staining (green), CD3 staining (red), DEC205 staining (green), and the coexistence of CD3 and DEC205 (yellow)) in the data of FIGS. 26(a) and 26(b) using Hybrid Cell Count program (manufactured by Keyence Corp.) are shown in FIGS. 27(a) and 27(b), respectively. In FIGS. 25 to 27, "no treatment" or "no treat." depicts the results obtained in an untreated group, "Cont." depicts the results obtained in the group treated with the anti-human CD20 CAR-expressing T cells, and 7×19 depicts the group treated with the anti-human CD20 CAR-IL-7/CCL19-expressing T cells.

(Results)

From the results of FIG. 25, the treatment with the anti-human CD20 CAR-IL-7/CCL19-expressing T cells accelerated necrosis (regions indicated by the arrows), and regions where the nuclei disappeared were observed. The results of FIGS. 26(a) and 27(a) demonstrated that T cells infiltrate into cancer tissues by the treatment with the anti-human CD20 CAR-IL-7/CCL19-expressing T cells. The results of FIGS. 26(b) and 27(b) demonstrated that dendritic cells together with the T cells infiltrate into cancer tissues by the treatment with the anti-human CD20 CAR-IL-7/CCL19-expressing T cells.

Example 10

[Therapeutic Effect Brought about by Combination of IL-7 and CCL19 on Tumor]

5×10⁵ P815-hCD20 cells were subcutaneously inoculated to each DBA/2 mouse. On day 3 post-inoculation, 1×10⁶ anti-human CD20 CAR-expressing T cells, anti-human CD20 CAR-IL-7-expressing T cells which expressed IL-7 alone as the immune function-enhancing factor (not expressing CCL19), anti-human CD20 CAR-CCL19-expressing T cells which expressed CCL19 alone as the immune function-enhancing factor (not expressing IL-7), or anti-human CD20 CAR-IL-7/CCL19-expressing T cells which expressed IL-7 and CCL19 were intravenously administered thereto. A control mouse group was established without administration of CAR-expressing T cells which expressed neither IL-7 nor CCL19. On day 10 post-administration, the major axis and the minor axis of tumor were measured, and the tumor volume (mm³) was calculated in the same way as above. The results are shown in FIG. 28. In FIG. 28, "No treat" depicts the results obtained without the administration of the CAR-expressing T cells, "Control CAR" depicts the results obtained by the administration of the anti-human CD20 CAR-expressing T cells, "IL-7 CAR" depicts the results obtained by the administration of the anti-human CD20 CAR-IL-7-expressing T cells, "CCL19 CAR" depicts the results obtained by the administration of the anti-human CD20 CAR-CCL19-expressing T cells, and "IL-7/CCL19 CAR" depicts the results obtained by the administration of the anti-human CD20 CAR-IL-7/CCL19-expressing T cells.

The anti-human CD20 CAR-IL-7-expressing T cells were obtained by preparing a pMSGV vector containing anti-human CD20 CAR-F2A-IL-7 (IL-7 expression-anti-human CD20 CAR vector) and transferring this vector to mouse T cells in the same way as in "Transduction of mouse T cells" of Example 1. Likewise, the anti-human CD20 CAR-CCL19-expressing T cells were obtained by preparing a pMSGV vector containing anti-human CD20 CAR-F2A-CCL19 (CCL19 expression-anti-human CD20 CAR vector) and transferring this vector to mouse T cells in the same way as in "Transduction of mouse T cells" of Example 1. The preparation of each vector was performed according to the method of "Preparation of anti-FITC CAR expression vector for expression of IL-7 and CCL19" or "Preparation of anti-CD20 CAR expression vector for expression of IL-7 and CCL19" of Example 1. A sequence of positions 1 to 462 and a stop codon following these positions in SEQ ID NO: 9 was used as a sequence encoding IL-7. A sequence of positions 538 to 864 in SEQ ID NO: 9 was used as a sequence encoding CCL19. The results are shown in FIG. 28.

(Results)

As shown in FIG. 28, the administration of the anti-human CD20 CAR-IL-7-expressing T cells or the anti-human CD20 CAR-CCL19-expressing T cells merely exhibited a tumor growth inhibitory effect equivalent to or slightly lower than that by the administration of the control anti-human CD20 CAR-expressing T cells, whereas the tumor almost disappeared by the administration of the anti-human CD20 CAR-IL-7/CCL19-expressing T cells. Thus, although IL-7 or CCL19 alone hardly has a tumor growth inhibitory effect, the combination of IL-7 and CCL19 was shown to produce a very high tumor growth inhibitory effect.

Example 11

[Cytotoxic Activity Against Tumor Cells in $^{51}$Cr Release Assay-1]

(Selection of T Cell Immune Function-Enhancing Factor)

In the microenvironment of cancer tissues, inhibitory signals are transduced to immunocytes so that antitumor immune response is inhibited to thereby attenuate the effect of immunotherapy. The inhibitory signals to immunocytes are transduced by SHP-1 or SHP-2. Thus, in the T cell therapy of cancer, the antitumor effect can be potentiated by allowing T cells themselves to produce a dominant negative mutant that inhibits the effect of SHP-1 or SHP-2. Accordingly, a vector for the coexpression of a dominant negative mutant inhibiting the effects of SHP-1 or SHP-2, and CAR was prepared, and cytotoxic activity against tumor cells was examined.

(Preparation of CAR Expression Vector for Expression of Dominant Negative Mutant of SHP1 or SHP2)

A DNA fragment encoding a dominant negative mutant of mouse SHP1 (SHP1DN) containing a mutation of a catalytic cysteine residue at position 453 to serine (C453S) was prepared by PCR-mediated site-directed mutagenesis. A DNA fragment encoding a dominant negative mutant of mouse SHP2 (SHP2DN) containing a mutation of a catalytic cysteine residue at position 459 to serine (C459S) was synthesized by Life Technologies Corp. and used. A nucleotide sequence encoding the mouse SHP1DN is shown in SEQ ID NO: 11, and a nucleotide sequence encoding the mouse SHP2DN is shown in SEQ ID NO: 12. 3 bases at positions 1357 to 1359 in SEQ ID NO: 11 and at positions 1375 to 1377 in SEQ ID NO: 12 are mutated sites. The DNA fragment encoding SHP1DN or SHP2DN were inserted to the MCS of the pMSGV vector containing anti-human CD20 scFv CAR-F2A-MCS in the course of the preparation of the IL-7/CCL19 expression-anti-human CD20 CAR vector in Example 2 to obtain a SHP1DN expression-anti-human CD20 CAR vector and a SHP2DN expression-anti-human CD20 CAR vector, respectively. The maps of the obtained vectors are shown in FIG. 29.

(Transduction of Mouse T Cells)

The SHP1DN expression-anti-human CD20 CAR vector or the SHP2DN expression-anti-human CD20 CAR vector was transferred to mouse T cells in the same way as in Example 1 to obtain anti-human CD20 CAR-SHP1DN-expressing T cells and anti-human CD20 CAR-SHP2DN-expressing T cells, respectively. The anti-human CD20 CAR-expressing T cells prepared in Example 1 were used as a control.

(Cytotoxic Activity Against Tumor Cells in $^{51}$Cr Release Assay)

The cytotoxic activity of the CAR-expressing T cells against tumor was measured by the standard 4-hour $^{51}$Cr release assay. P815 expressing human CD20 (P815-hCD20) was used as target tumor cells. The tumor cells were collected, cultured at 37° C. for 1 hour in the presence of 100 μCi Na$_2$$^{51}$CrO$_4$, and then washed three times. Then, the tumor cells were cocultured with the anti-human CD20 CAR-expressing T cells, the anti-human CD20 CAR-SHP1DN-expressing T cells, or the anti-human CD20 CAR-SHP2DN-expressing T cells as effector T cells. The effector/target ratio was set to 0.6, 1.25, 2.5, 5, or 10. The maximum release and spontaneous release of the target cells were measured by culturing the cells in a culture medium containing 10% Triton-X (manufactured by Sigma-Aldrich Co. LLC.) or the culture medium alone. The $^{51}$Cr release of the supernatant was measured using TopCount scintillation counter (manufactured by PerkinElmer, Inc.). The percentage of specific cytotoxicity was calculated according to the equation: Specific cytotoxicity (%)=[(Test release−Spontaneous release)/(Maximum release−Spontaneous release)]× 100. The results are shown in FIG. 30. In FIG. 30(a), the open circle depicts the results about the anti-human CD20 CAR-expressing T cells, and the filled circle depicts the results about the anti-human CD20 CAR-SHP1DN-expressing T cells. In FIG. 30(b), the open circle depicts the results about the anti-human CD20 CAR-expressing T cells, and the filled circle depicts the results about the anti-human CD20 CAR-SHP2DN-expressing T cells. The abscissa indicates the ratio between the effector (T cells) and the target (tumor cells) by an E/T ratio, and the ordinate shows the specific cytotoxicity (%). Statistically significant difference was studied by the Student's t-test (* p<0.05).

As shown in FIG. 30, the anti-human CD20 CAR-SHP1DN-expressing T cells and the anti-human CD20 CAR-SHP2DN-expressing T cells were shown to have significantly higher cytotoxic activity against tumor cells than that of the anti-human CD20 CAR-expressing T cells.

Example 12

[Cytotoxic Activity Against Tumor Cells in $^{51}$Cr Release Assay-2]

P815-hCD20 (1×10$^4$ cells/well) was mixed with the anti-FITC CAR-expressing T cells (Cont., circle) or the anti-FITC CAR-IL-7/CCL19-expressing T cells (7×19, square) at an effector/target (E/T) ratio of 0.15625, 0.3125, 0.625, 2.5, 5, or 10 in the presence of unlabeled (Ab, open) or FITC-bound (FITC-Ab, filled) rituximab. In the same way as above, the $^{51}$Cr release of the supernatant was measured, and the percentage of cytotoxic activity was calculated. The results are shown in FIG. 31. In FIG. 31, the "filled circle" depicts the results obtained by the mixing with the anti-FITC CAR-expressing T cells in the presence of FITC-bound rituximab, the "open circle" depicts the results obtained by the mixing with the anti-FITC CAR-expressing T cells in the presence of unlabeled rituximab, the "filled square" depicts the results obtained by the mixing with the anti-FITC CAR-IL-7/CCL19-expressing T cells in the presence of FITC-bound rituximab, and the "open square" depicts the results obtained by the mixing with the anti-FITC CAR-IL-7/CCL19-expressing T cells in the presence of unlabeled rituximab.

815-hCD20 (1×10$^4$ cells/well) was mixed with the anti-human CD20 CAR-expressing T cells or the anti-human CD20 CAR-IL-7/CCL19-expressing T cells at an effector/target (E/T) ratio of 0.3125, 0.625, 2.5, 5, 10, or 20. In the same way as above, the $^{51}$Cr release of the supernatant was measured, and the percentage of cytotoxic activity was calculated. The results are shown in FIG. 32. In FIG. 32, the "filled circle" depicts the results obtained by the mixing with the anti-human CD20 CAR-IL-7/CCL19-expressing T cells, and the "open circle" depicts the results obtained by the mixing with the anti-human CD20 CAR-expressing T cells.

(Results)

As shown in FIGS. 31 and 32, the anti-FITC CAR-IL-7/CCL19-expressing T cells were shown to maintain cytotoxic activity per cell against tumor cells at the same level as that of the anti-FITC CAR-expressing T cells. Likewise, the anti-human CD20 CAR-IL-7/CCL19-expressing T cells were shown to maintain cytotoxic activity per cell against tumor cells at the same level as that of the anti-human CD20 CAR-expressing T cells.

Example 13

[In Vivo Survival of CAR-Expressing T Cells and Differentiation into Memory T Cells]

(Flow Cytometry Analysis)

5×10$^5$ P815-hCD20 cells were subcutaneously inoculated to each DBA/2 mouse. On day 10 post-inoculation, an anticancer agent cyclophosphamide (CPA, 100 mg/kg) was intraperitoneally administered thereto, and on day 14, 1×10$^6$ anti-human CD20 CAR-IL-7/CCL19-expressing T cells or anti-human CD20 CAR-expressing T cells were intravenously administered thereto. On day 21 post-administration of the CAR-expressing T cells, leukocytes were isolated from the spleen or regional lymph nodes of tumor (subaxillary area, upper arm, and groin). The results of analyzing CD4, CD8, CD44, and CD62L for the surface phenotypes of the leukocytes by flow cytometry are shown in FIG. 33. The spleen leukocytes were stimulated by culture for 4 days with P815-hCD20 treated with mitomycin C. The results of examining the proliferation of T cells by flow cytometry are shown in FIG. 34. The expression of CAR was confirmed using biotinylated protein L and APC-bound streptavidin. In FIG. 33, the numerals represent the ratios of the respective regions gated upon CD4$^+$ T cells and CD8$^+$ T cells (CD62L$^+$CD44$^-$: naive T cells, CD62L$^+$CD44$^+$: central memory T cells, CD62L$^-$CD44$^+$: effector memory T cells). In FIG. 34, the numerals represent the ratio of protein L-positive T cells. In FIGS. 33 and 34, "Cont." depicts the results about the anti-human CD20 CAR-expressing T cells, and "7×19" depicts the results about the anti-human CD20 CAR-IL-7/CCL19-expressing T cells.

(Results)

The results shown in FIGS. 33 and 34 demonstrated that the memory T cells are increased in the spleens and lymph nodes of the mice given the anti-human CD20 CAR-IL-7/CCL19-expressing T cells, and the anti-human CD20 CAR-IL-7/CCL19-expressing T cells that survive in the mice proliferate strongly by coculture with the tumor cells expressing human CD20. Together with the results of the survival rate in FIGS. 21 and 22, these results suggest that the CAR-expressing T cells of the present invention survive efficiently in vivo in a recipient and also have the ability to extinguish cancer cells and enhance a survival rate by becoming memory T cells, and indicated that the CAR-expressing T cells of the present invention are also effective for the prevention of cancer recurrence.

INDUSTRIAL APPLICABILITY

Use of the CAR expression vector of the present invention enables the preparation of CAR-T cells having both of viability and the ability to accumulate lymphocytes, and CAR-T cells having resistance to immunosuppression in a cancer microenvironment. Therefore, the CAR expression vector of the present invention is applicable to the field of cancer immunotherapy.

The invention claimed is:

1. A CAR expression vector comprising a nucleic acid encoding a chimeric antigen receptor (CAR) and a nucleic acid encoding a T cell immune function-enhancing factor, wherein the nucleic acid encoding the T cell immune function-enhancing factor consists of a nucleic acid encoding interleukin-7 and a nucleic acid encoding CCL19.

2. The CAR expression vector according to claim 1, wherein the nucleic acid encoding the CAR and the nucleic acid encoding the T cell immune function-enhancing factor are linked via a sequence encoding a self-cleaving peptide.

3. The CAR expression vector according to claim 1, wherein the nucleic acid encoding interleukin-7 and the nucleic acid encoding CCL19 are linked via a sequence encoding a self-cleaving peptide.

4. The CAR expression vector according to claim 1, wherein the nucleic acid encoding the CAR contains a nucleic acid encoding a polypeptide of a single chain antibody that recognizes FITC or CD20.

5. The CAR expression vector according to claim 1, wherein the nucleic acid encoding the CAR contains a nucleic acid encoding a polypeptide of a CD8 transmembrane region.

6. The CAR expression vector according to claim 1, wherein the nucleic acid encoding the CAR contains nucleic acids encoding polypeptides of a CD28 intracellular region, a 4-1BB intracellular region, and a CD3 intracellular region.

7. An isolated CAR-expressing T cell, or a culture comprising the isolated CAR-expressing T cell, said isolated T cell prepared by introducing the CAR expression vector according to claim 1, and expressing the CAR, interleukin-7, and CCL19.

8. An isolated CAR-expressing T cell, or a culture comprising the isolated CAR-expressing T cell, said isolated T cell prepared by introducing the CAR expression vector according to claim 2, and expressing the CAR, interleukin-7, and CCL19.

9. An isolated CAR-expressing T cell, or a culture comprising the isolated CAR-expressing T cell, said isolated T cell prepared by introducing the CAR expression vector according to claim 3, and expressing the CAR, interleukin-7, and CCL19.

10. An isolated CAR-expressing T cell, or a culture comprising the isolated CAR-expressing T cell, said isolated T cell prepared by introducing the CAR expression vector according to claim 4, and expressing the CAR, interleukin-7, and CCL19.

11. An isolated CAR-expressing T cell, or a culture comprising the isolated CAR-expressing T cell, said isolated T cell prepared by introducing a CAR expression vector that expresses a nucleic acid encoding a CAR and a nucleic acid encoding a first T cell immune function-enhancing factor, said first T cell immune function-enhancing factor consisting of interleukin-7, and a CAR expression vector that expresses a nucleic acid encoding a CAR and a nucleic acid encoding a second T cell immune function-enhancing factor, said second T cell immune function-enhancing factor consisting of CCL19; and expressing the CAR, interleukin-7, and CCL19.

12. An anticancer agent comprising the isolated CAR-expressing T cell according to claim 7 and a pharmaceutically acceptable additive.

13. An anticancer agent comprising the isolated CAR-expressing T cell according to claim 8 and a pharmaceutically acceptable additive.

14. An anticancer agent comprising the isolated CAR-expressing T cell according to claim 9 and a pharmaceutically acceptable additive.

15. An anticancer agent comprising the isolated CAR-expressing T cell according to claim 10 and a pharmaceutically acceptable additive.

16. An anticancer agent comprising the isolated CAR-expressing T cell according to claim 11 and a pharmaceutically acceptable additive.

17. The CAR expression vector of claim 1 wherein said interleukin-7 is human interleukin-7 and said CCL19 is human CCL19.

18. The isolated CAR-expressing T cell or cell culture of claim 7, wherein said interleukin-7 is human interleukin-7 and said CCL19 is human CCL19.

19. The isolated CAR-expressing T cell or cell culture of claim 11, wherein said interleukin-7 is human interleukin-7 and said CCL19 is human CCL19.

* * * * *

UNITED STATES PATENT AND TRADEMARK OFFICE
CERTIFICATE OF CORRECTION

PATENT NO. : 10,316,102 B2
APPLICATION NO. : 15/513870
DATED : June 11, 2019
INVENTOR(S) : Koji Tamada, Yukimi Sakoda and Keishi Adachi Page 1 of 1

It is certified that error appears in the above-identified patent and that said Letters Patent is hereby corrected as shown below:

In the Claims

Column 43, Claim 6, Line 39, "ζ" is missing after "CD3".

Signed and Sealed this
Twenty-second Day of October, 2019

Andrei Iancu
*Director of the United States Patent and Trademark Office*